US009688757B2

(12) United States Patent
Nedospasov et al.

(10) Patent No.: US 9,688,757 B2
(45) Date of Patent: Jun. 27, 2017

(54) BI-SPECIFIC AFFINITY REAGENTS FOR CELL-LINEAGE-SPECIFIC TNF-ALPHA NEUTRALIZATION

(71) Applicants: Deutsches Rheuma-Forschungszentrum Berlin, Berlin (DE); Engelhardt Institute of Molecular Biology, Moscow (RU)

(72) Inventors: Sergei Nedospasov, Berlin (DE); Andrey Kruglov, Berlin (DE); Grigory Alexandrovich Efimov, Moscow (RU)

(73) Assignee: DEUTSCHES RHEUMA-FORSCHUNGSZENTRUM BERLIN, Berlin (DE)

( * ) Notice: Subject to any disclaimer, the term of this patent is extended or adjusted under 35 U.S.C. 154(b) by 0 days.

(21) Appl. No.: 14/438,288

(22) PCT Filed: Oct. 28, 2013

(86) PCT No.: PCT/EP2013/072470
§ 371 (c)(1),
(2) Date: Apr. 24, 2015

(87) PCT Pub. No.: WO2014/064287
PCT Pub. Date: May 1, 2014

(65) Prior Publication Data
US 2015/0284460 A1 Oct. 8, 2015

(30) Foreign Application Priority Data
Oct. 26, 2012 (EP) .................................... 12190112

(51) Int. Cl.
| C07K 16/24 | (2006.01) |
| C07K 16/28 | (2006.01) |
| A61K 39/395 | (2006.01) |
| C12N 15/13 | (2006.01) |
| C07K 16/46 | (2006.01) |
| A61K 39/00 | (2006.01) |

(52) U.S. Cl.
CPC ............ *C07K 16/28* (2013.01); *C07K 16/241* (2013.01); *C07K 16/2803* (2013.01); *C07K 16/468* (2013.01); *A61K 2039/505* (2013.01); *C07K 2317/22* (2013.01); *C07K 2317/31* (2013.01); *C07K 2317/565* (2013.01); *C07K 2317/569* (2013.01); *C07K 2317/622* (2013.01); *C07K 2317/76* (2013.01)

(58) Field of Classification Search
None
See application file for complete search history.

(56) References Cited

FOREIGN PATENT DOCUMENTS

| WO | 2006063150 A2 | 6/2006 |
| WO | 2008003116 A2 | 1/2008 |

OTHER PUBLICATIONS

Diseases & Conditions, American Academy of Rheumatology [online], [retrieved on Aug. 29, 2016]. Retrieved from the Internet: <URL:http://www.rheumatology.org/I-Am-A/Patient-Caregiver/Diseases-Conditions>.*
Jordana et al. Immune-inflammatory functions of fibroblasts. Eur Respir J. Dec. 1994;7(12):2212-22.*
Agusti et al. Evaluation of COPD Longitudinally to Identify Predictive Surrogate Endpoints (ECLIPSE) Investigators. Persistent systemic inflammation is associated with poor clinical outcomes in COPD: a novel phenotype. PLoS One. 2012;7(5):e37483. Epub May 18, 2012.*
Rudikoff et al. "Single Amino acid substitution altering antigen-binding specificity" Proceedings of the National Academy of Science, 1982, vol. 79, pp. 1979-1983.*
MaCallum et al. "Antibody-antigen Interactions: Contact Analysis and Binding Site Topography" Journal of Molecular biology, vol. 262, pp. 732-745.*
De Pascalis et al. "Grafting of Abbreviated Complementarity-Determining Regions Containing Specificity-Determining Residues Essential for Ligand Contact to engineer a Less Immunogenic Humanized Monoclonal Antibody" The Journal of Immunology, 2002, vol. 169, pp. 3076-3084.*
Vajdos et al. "Comprehensive Functional Maps of the antigen-binding Site of an Anti-ErbB2 Antibody Obtained with Shotgun Scanning Mutagenesis" Journal of Molecular Biology, 2002, vol. 320, pp. 415-428.*
Holm et al. "Functional mapping and single chain construction of the anti-cytokeratin 8 monoclonal antibody TS1", Molecular Immunology, 2007, vol. 44, pp. 1075-1084.*
Chen et al. "Selection and Analysis of an Optimized Anti-VEGF Antibody: Crystal Structure of an Affinity-matured Fab in Complex with Antigen", Journal of Molecular Biology, 1999, vol. 293, pp. 865-881.*
Wu et al. "Humanization of a Murine Monoclonal Antibody by Simultaneous Optimization of Framework and CDR Residues" Journal of Molecular Biology, 1999, vol. 294, pp. 151-162.*
Casset et al. "A peptide mimetic of an anti-CD4 monoclonal antibody by rational design" Biochemical and Biophysical Research Communications, 2003, vol. 307, pp. 198-205.*
Kanakaraj et al., "Simultaneous targeting of TNF and Ang2 with a novel bispecific antibody enhances efficacy in an in vivo model of arthritis," in MABS Sep.-Oct. 2012, vol. 4(5), Sep. 2012, pp. 600-613.
Bongartz et al., "Anti-TNF antibody therapy in rheumatoid arthritis and the risk of serious infections and malignancies: systematic review and meta-analysis of rare harmful effects in randomized controlled trials.," in JAMA: The Journal of the American Medical Association May 17, 2006, vol. 265(19), May 17, 2006, pp: 2275-2285.

(Continued)

*Primary Examiner* — David Romeo
(74) *Attorney, Agent, or Firm* — Joyce von Natzmer; Agris & von Natzmer, LLP

(57) ABSTRACT

The invention relates to isolated bispecific affinity reagents, such as antibodies or antibody fragments that bind TNFα and a marker molecule for macrophages and/or neutrophils. The affinity reagents of the invention enable pathogenic sub-populations of TNFα to be neutralized, while protective sub-populations of TNFα are not affected.

19 Claims, 15 Drawing Sheets

(56) References Cited

OTHER PUBLICATIONS

Figure 1:
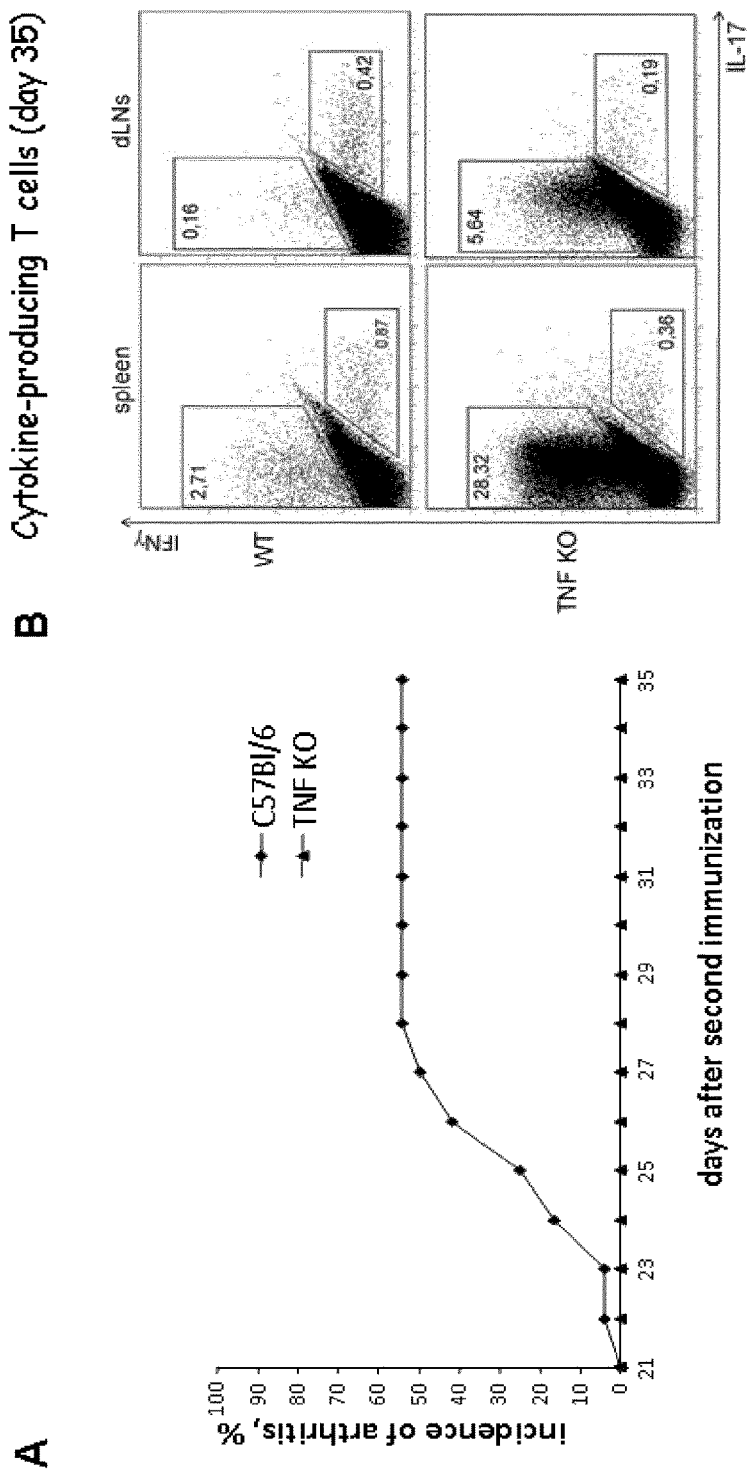

Herenius et al., "Monocyte migration to the synovium in rheumatoid arthritis patients treated with adalimumab," in Annals of the Rheumatic Diseases Jun. 2011, vol. 70(6), Jun. 2011, pp. 1160-1162.

* cited by examiner

B

Fig. 6
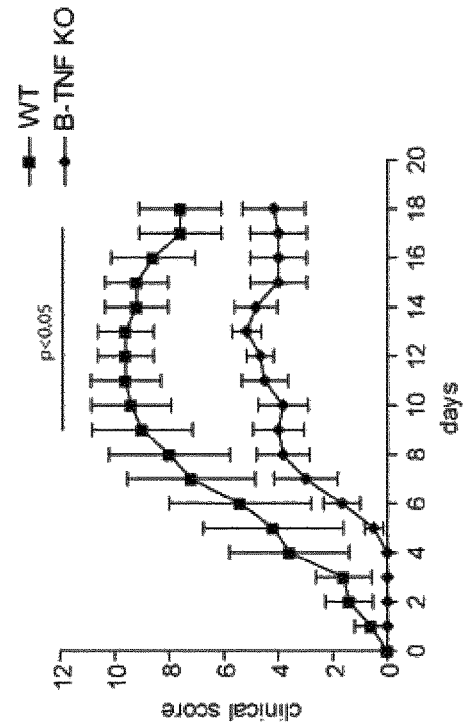
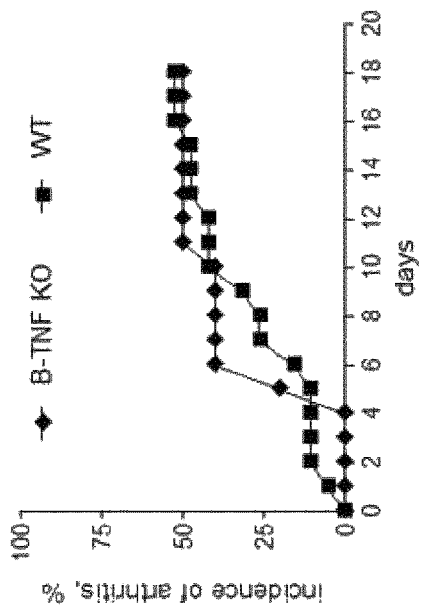

Fig. 8
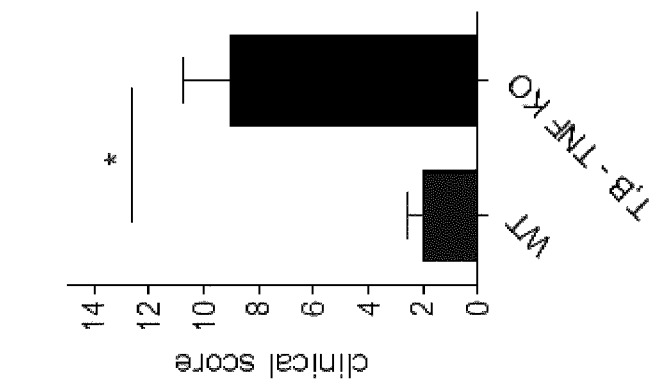
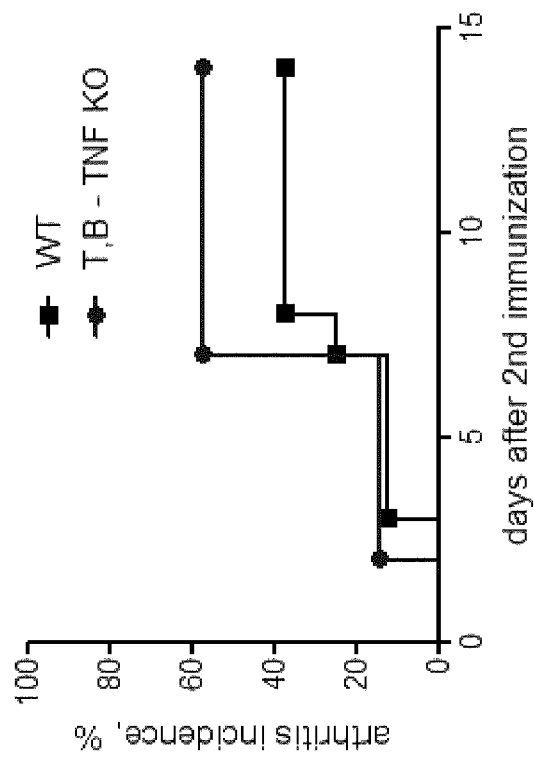

Fig. 14

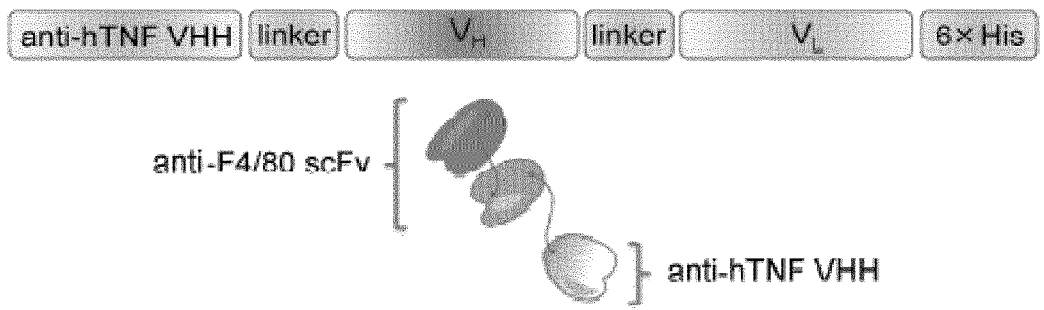

Amino acid sequence:

MGSQVQLQESGGGLVQPGGSLRLSCAASGRTFSDHSGYTYTIGWFRQAPGKEREFVARIYWSSGNTYYA
DSVKGRFAISRDIAKNTVDLTMNNLEPEDTAVYYCAARDGIPTSRSVESYNYWGQGTQVTVSSAGAGSG
GGGSGMQVQLQQSGAELVKPGTSVKLSCKASGYTFTNHMNWVKQTTGQGLEWIGRINPGTGGTSYNV
NFKGKATLTVDESSSTAFMQLSSLTPEDSAVYYCARGDSYWYFDFWGPGTMVTVSGSGGGGSGGGGSG
GGGSDVQMTQSPYNLVASPGESVSINCKASKSISKYLAWYQQKPGKANKLLIYEGSTLQSGIPSRFSGSGS
GTDFTLTIRSLEPEDFGLYYCQQHNEYPLTFGSGTKLEIKRADAAPTVAAAPRGGPEQKLISEEDLNSAVDLE
HHHHHH

Fig. 15
A
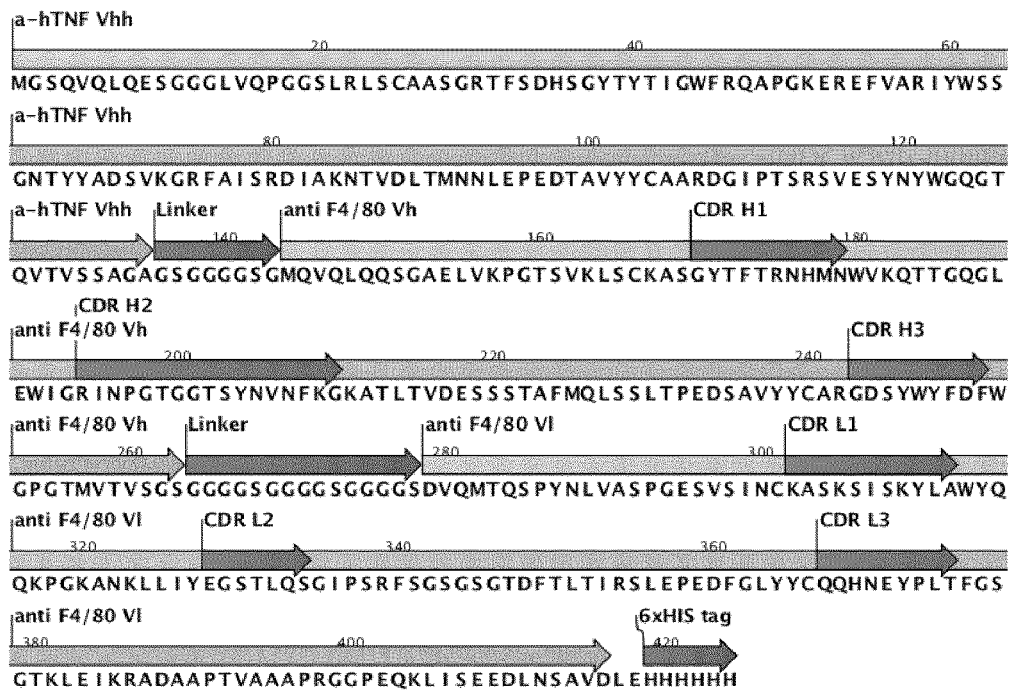
B
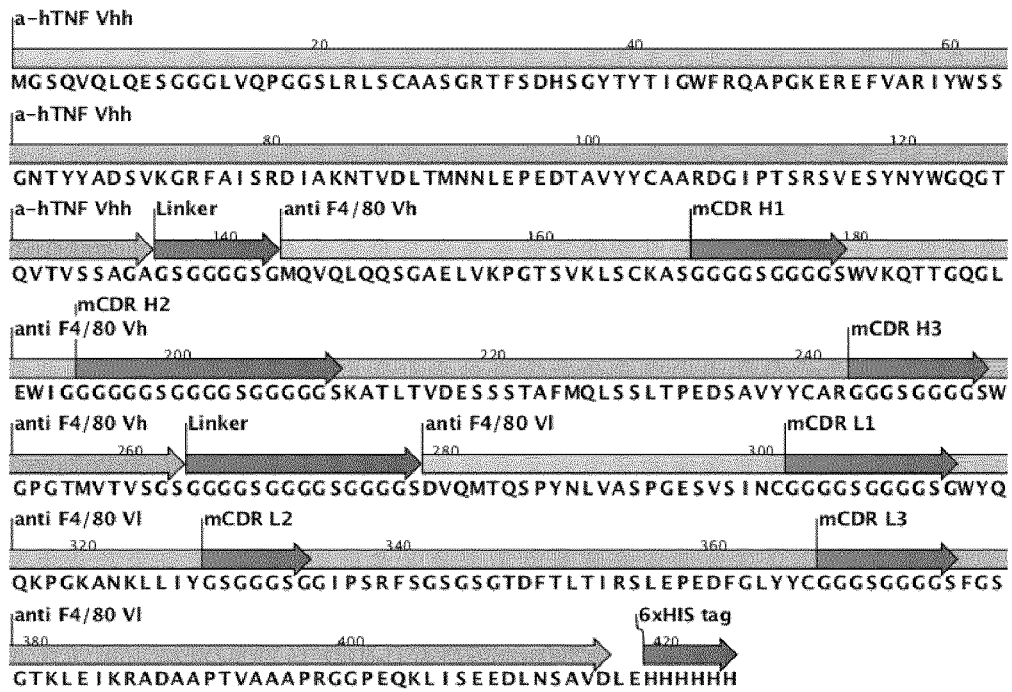

SEQUENCE LISTING

```
<160> NUMBER OF SEQ ID NOS: 22

<210> SEQ ID NO 1
<211> LENGTH: 135
<212> TYPE: PRT
<213> ORGANISM: Artificial
<220> FEATURE:
```

<223> OTHER INFORMATION: Antibody fragment

<400> SEQUENCE: 1

Met Gly Ser Gln Val Gln Leu Gln Glu Ser Gly Gly Gly Leu Val Gln
1               5                   10                  15

Pro Gly Gly Ser Leu Arg Leu Ser Cys Ala Ala Ser Gly Arg Thr Phe
            20                  25                  30

Ser Asp His Ser Gly Tyr Thr Tyr Thr Ile Gly Trp Phe Arg Gln Ala
        35                  40                  45

Pro Gly Lys Glu Arg Glu Phe Val Ala Arg Ile Tyr Trp Ser Ser Gly
    50                  55                  60

Asn Thr Tyr Tyr Ala Asp Ser Val Lys Gly Arg Phe Ala Ile Ser Arg
65                  70                  75                  80

Asp Ile Ala Lys Asn Thr Val Asp Leu Thr Met Asn Asn Leu Glu Pro
                85                  90                  95

Glu Asp Thr Ala Val Tyr Tyr Cys Ala Ala Arg Asp Gly Ile Pro Thr
            100                 105                 110

Ser Arg Ser Val Glu Ser Tyr Asn Tyr Trp Gly Gln Gly Thr Gln Val
        115                 120                 125

Thr Val Ser Ser Ala Gly Ala
    130                 135

<210> SEQ ID NO 2
<211> LENGTH: 9
<212> TYPE: PRT
<213> ORGANISM: Artificial
<220> FEATURE:
<223> OTHER INFORMATION: Antibody fragment

<400> SEQUENCE: 2

Gly Tyr Thr Phe Thr Asn His Met Asn
1               5

<210> SEQ ID NO 3
<211> LENGTH: 17
<212> TYPE: PRT
<213> ORGANISM: Artificial
<220> FEATURE:
<223> OTHER INFORMATION: Antibody fragment

<400> SEQUENCE: 3

Arg Ile Asn Pro Gly Thr Gly Thr Ser Tyr Asn Val Asn Phe Lys
1               5                   10                  15

Gly

<210> SEQ ID NO 4
<211> LENGTH: 9
<212> TYPE: PRT
<213> ORGANISM: Artificial
<220> FEATURE:
<223> OTHER INFORMATION: Antibody fragment

<400> SEQUENCE: 4

Gly Asp Ser Tyr Trp Tyr Phe Asp Phe
1               5

<210> SEQ ID NO 5
<211> LENGTH: 11
<212> TYPE: PRT
<213> ORGANISM: Artificial
<220> FEATURE:
<223> OTHER INFORMATION: Antibody fragment

<400> SEQUENCE: 5

Lys Ala Ser Lys Ser Ile Ser Lys Tyr Leu Ala
1               5                   10

<210> SEQ ID NO 6
<211> LENGTH: 7
<212> TYPE: PRT
<213> ORGANISM: Artificial
<220> FEATURE:
<223> OTHER INFORMATION: Antibody fragment

<400> SEQUENCE: 6

Glu Gly Ser Thr Leu Gln Ser
1               5

<210> SEQ ID NO 7
<211> LENGTH: 9
<212> TYPE: PRT
<213> ORGANISM: Artificial
<220> FEATURE:
<223> OTHER INFORMATION: Antibody fragment

<400> SEQUENCE: 7

Gln Gln His Asn Glu Tyr Pro Leu Thr
1               5

<210> SEQ ID NO 8
<211> LENGTH: 119
<212> TYPE: PRT
<213> ORGANISM: Artificial
<220> FEATURE:
<223> OTHER INFORMATION: Antibody fragment

<400> SEQUENCE: 8

Met Gln Val Gln Leu Gln Gln Ser Gly Ala Glu Leu Val Lys Pro Gly
1               5                   10                  15

Thr Ser Val Lys Leu Ser Cys Lys Ala Ser Gly Tyr Thr Phe Thr Asn
            20                  25                  30

His Met Asn Trp Val Lys Gln Thr Thr Gly Gln Gly Leu Glu Trp Ile
        35                  40                  45

Gly Arg Ile Asn Pro Gly Thr Gly Thr Ser Tyr Asn Val Asn Phe
    50                  55                  60

Lys Gly Lys Ala Thr Leu Thr Val Asp Glu Ser Ser Thr Ala Phe
65                  70                  75                  80

Met Gln Leu Ser Ser Leu Thr Pro Glu Asp Ser Ala Val Tyr Tyr Cys
                85                  90                  95

Ala Arg Gly Asp Ser Tyr Trp Tyr Phe Asp Phe Trp Gly Pro Gly Thr
            100                 105                 110

Met Val Thr Val Ser Gly Ser
        115

<210> SEQ ID NO 9
<211> LENGTH: 138
<212> TYPE: PRT
<213> ORGANISM: Artificial
<220> FEATURE:
<223> OTHER INFORMATION: Antibody fragment

<400> SEQUENCE: 9

Asp Val Gln Met Thr Gln Ser Pro Tyr Asn Leu Val Ala Ser Pro Gly
1               5                   10                  15

```
Glu Ser Val Ser Ile Asn Cys Lys Ala Ser Lys Ser Ile Ser Lys Tyr
             20                  25                  30

Leu Ala Trp Tyr Gln Gln Lys Pro Gly Lys Ala Asn Lys Leu Leu Ile
         35                  40                  45

Tyr Glu Gly Ser Thr Leu Gln Ser Gly Ile Pro Ser Arg Phe Ser Gly
 50                  55                  60

Ser Gly Ser Gly Thr Asp Phe Thr Leu Thr Ile Arg Ser Leu Glu Pro
 65                  70                  75                  80

Glu Asp Phe Gly Leu Tyr Tyr Cys Gln Gln His Asn Glu Tyr Pro Leu
                 85                  90                  95

Thr Phe Gly Ser Gly Thr Lys Leu Glu Ile Lys Arg Ala Asp Ala Ala
             100                 105                 110

Pro Thr Val Ala Ala Pro Arg Gly Gly Pro Glu Gln Lys Leu Ile
             115                 120                 125

Ser Glu Glu Asp Leu Asn Ser Ala Val Asp
             130                 135
```

<210> SEQ ID NO 10
<211> LENGTH: 415
<212> TYPE: PRT
<213> ORGANISM: Artificial
<220> FEATURE:
<223> OTHER INFORMATION: Antibody fragment

<400> SEQUENCE: 10

```
Met Gly Ser Gln Val Gln Leu Gln Glu Ser Gly Gly Gly Leu Val Gln
 1               5                   10                  15

Pro Gly Gly Ser Leu Arg Leu Ser Cys Ala Ala Ser Gly Arg Thr Phe
             20                  25                  30

Ser Asp His Ser Gly Tyr Thr Tyr Thr Ile Gly Trp Phe Arg Gln Ala
         35                  40                  45

Pro Gly Lys Glu Arg Glu Phe Val Ala Arg Ile Tyr Trp Ser Ser Gly
 50                  55                  60

Asn Thr Tyr Tyr Ala Asp Ser Val Lys Gly Arg Phe Ala Ile Ser Arg
 65                  70                  75                  80

Asp Ile Ala Lys Asn Thr Val Asp Leu Thr Met Asn Asn Leu Glu Pro
                 85                  90                  95

Glu Asp Thr Ala Val Tyr Tyr Cys Ala Ala Arg Asp Gly Ile Pro Thr
             100                 105                 110

Ser Arg Ser Val Glu Ser Tyr Asn Tyr Trp Gly Gln Gly Thr Gln Val
             115                 120                 125

Thr Val Ser Ser Ala Gly Ala Gly Ser Gly Gly Gly Gly Ser Gly Met
             130                 135                 140

Gln Val Gln Leu Gln Gln Ser Gly Ala Glu Leu Val Lys Pro Gly Thr
145                 150                 155                 160

Ser Val Lys Leu Ser Cys Lys Ala Ser Gly Tyr Thr Phe Thr Asn His
             165                 170                 175

Met Asn Trp Val Lys Gln Thr Thr Gly Gln Gly Leu Glu Trp Ile Gly
             180                 185                 190

Arg Ile Asn Pro Gly Thr Gly Gly Thr Ser Tyr Asn Val Asn Phe Lys
             195                 200                 205

Gly Lys Ala Thr Leu Thr Val Asp Glu Ser Ser Thr Ala Phe Met
             210                 215                 220

Gln Leu Ser Ser Leu Thr Pro Glu Asp Ser Ala Val Tyr Tyr Cys Ala
225                 230                 235                 240
```

```
Arg Gly Asp Ser Tyr Trp Tyr Phe Asp Phe Trp Gly Pro Gly Thr Met
            245                 250                 255
Val Thr Val Ser Gly Ser Gly Gly Gly Ser Gly Gly Gly Gly Ser
        260                 265                 270
Gly Gly Gly Gly Ser Asp Val Gln Met Thr Gln Ser Pro Tyr Asn Leu
            275                 280                 285
Val Ala Ser Pro Gly Glu Ser Val Ser Ile Asn Cys Lys Ala Ser Lys
        290                 295                 300
Ser Ile Ser Lys Tyr Leu Ala Trp Tyr Gln Gln Lys Pro Gly Lys Ala
305                 310                 315                 320
Asn Lys Leu Leu Ile Tyr Glu Gly Ser Thr Leu Gln Ser Gly Ile Pro
                325                 330                 335
Ser Arg Phe Ser Gly Ser Gly Ser Gly Thr Asp Phe Thr Leu Thr Ile
            340                 345                 350
Arg Ser Leu Glu Pro Glu Asp Phe Gly Leu Tyr Tyr Cys Gln Gln His
        355                 360                 365
Asn Glu Tyr Pro Leu Thr Phe Gly Ser Gly Thr Lys Leu Glu Ile Lys
        370                 375                 380
Arg Ala Asp Ala Ala Pro Thr Val Ala Ala Pro Arg Gly Gly Pro
385                 390                 395                 400
Glu Gln Lys Leu Ile Ser Glu Glu Asp Leu Asn Ser Ala Val Asp
                405                 410                 415

<210> SEQ ID NO 11
<211> LENGTH: 405
<212> TYPE: DNA
<213> ORGANISM: Artificial
<220> FEATURE:
<223> OTHER INFORMATION: Antibody fragment DNA

<400> SEQUENCE: 11
atgggttccc aagttcagct tcaagaatct ggtggaggac ttgttcaacc tggtggatct      60
cttaggcttt cttgcgctgc ttctggaagg actttctctg atcactctgg atacacttac     120
actattggat ggttcagaca ggctccagga aaagagagag agttcgttgc taggatctac     180
tggtcatctg gaaacactta ctacgctgat tctgtgaagg gaagattcgc tatttctagg     240
gatattgcta agaacactgt ggatcttact atgaacaacc ttgagccaga ggatactgct     300
gtttactatt gcgctgctag ggatggaatt ccaacttcta gatctgtgga gtcttacaac     360
tactggggac agggaactca agtgactgtt tcttctgccg gcgcg                     405

<210> SEQ ID NO 12
<211> LENGTH: 30
<212> TYPE: DNA
<213> ORGANISM: Artificial
<220> FEATURE:
<223> OTHER INFORMATION: Antibody fragment DNA

<400> SEQUENCE: 12
ggttatacct ttacccgcaa tcatatgaat                                        30

<210> SEQ ID NO 13
<211> LENGTH: 51
<212> TYPE: DNA
<213> ORGANISM: Artificial
<220> FEATURE:
<223> OTHER INFORMATION: Antibody fragment DNA

<400> SEQUENCE: 13
```
cgtattaatc cgggtacagg tggcaccagc tataatgtga attttaaagg c         51

<210> SEQ ID NO 14
<211> LENGTH: 27
<212> TYPE: DNA
<213> ORGANISM: Artificial
<220> FEATURE:
<223> OTHER INFORMATION: Antibody fragment DNA

<400> SEQUENCE: 14
ggcgatagct attggtattt tgatttt                                    27

<210> SEQ ID NO 15
<211> LENGTH: 33
<212> TYPE: DNA
<213> ORGANISM: Artificial
<220> FEATURE:
<223> OTHER INFORMATION: Antibody fragment DNA

<400> SEQUENCE: 15
aaagccagca aaagcattag caaatatctg gca                             33

<210> SEQ ID NO 16
<211> LENGTH: 21
<212> TYPE: DNA
<213> ORGANISM: Artificial
<220> FEATURE:
<223> OTHER INFORMATION: Antibody fragment DNA

<400> SEQUENCE: 16
gaaggtagca ccctgcagag c                                          21

<210> SEQ ID NO 17
<211> LENGTH: 27
<212> TYPE: DNA
<213> ORGANISM: Artificial
<220> FEATURE:
<223> OTHER INFORMATION: Antibody fragment DNA

<400> SEQUENCE: 17
cagcagcata atgaatatcc gctgacc                                    27

<210> SEQ ID NO 18
<211> LENGTH: 360
<212> TYPE: DNA
<213> ORGANISM: Artificial
<220> FEATURE:
<223> OTHER INFORMATION: Antibody fragment DNA

<400> SEQUENCE: 18
atgcaggttc agctgcagca gagcggtgca gaactggtta aaccgggtac aagcgttaaa    60
ctgagctgta aagcaagcgg ttatacccttt acccgcaatc atatgaattg ggtgaaacag   120
accaccggtc agggtctgga atggattggt cgtattaatc cgggtacagg tggcaccagc   180
tataatgtga attttaaagg caaagcaacc ctgaccgttg atgaaagcag cagcaccgca   240
tttatgcagc tgagcagcct gacaccggaa gatagcgcag tgtactactg tgcacgtggc   300
gatagctatt ggtattttga ttttggggt ccgggtacaa tggttaccgt tagcggtagc    360

<210> SEQ ID NO 19
<211> LENGTH: 415
<212> TYPE: DNA
<213> ORGANISM: Artificial
<220> FEATURE:
<223> OTHER INFORMATION: Antibody fragment DNA

<400> SEQUENCE: 19

```
gatgttcaga tgacccagag cccgtataat ctggttgcat ctccgggtga aagcgttagc    60
attaattgca aagccagcaa aagcattagc aaatatctgg catggtatca gcagaaaccg   120
ggtaaagcaa ataaactgct gatttatgaa ggtagcaccc tgcagagcgg tattccgagc   180
cgttttagcg gttctggtag cggcaccgat tttaccctga ccattcgtag cctggaaccg   240
gaagattttg gtctgtatta ttgccagcag cataatgaat atccgctgac ctttggtagc   300
ggtacaaaac tggaaattaa acgtgcagat gcagcaccga ccgttgcagc agctccgcgt   360
ggtggtccgg aacagaaact gattagcgaa gaagatctga atagcgcagt tgatc        415
```

<210> SEQ ID NO 20
<211> LENGTH: 1249
<212> TYPE: DNA
<213> ORGANISM: Artificial
<220> FEATURE:
<223> OTHER INFORMATION: Antibody fragment DNA

<400> SEQUENCE: 20

```
atgggttccc aagttcagct tcaagaatct ggtggaggac ttgttcaacc tggtggatct    60
cttaggcttt cttgcgctgc ttctggaagg actttctctg atcactctgg atacacttac   120
actattggat ggttcagaca ggctccagga aaagagagag agttcgttgc taggatctac   180
tggtcatctg gaaacactta ctacgctgat tctgtgaagg gaagattcgc tatttctagg   240
gatattgcta agaacactgt ggatcttact atgaacaacc ttgagccaga ggatactgct   300
gtttactatt gcgctgctag ggatggaatt ccaacttcta gatctgtgga gtcttacaac   360
tactggggac agggaactca agtgactgtt tcttctgccg gcgcgggatc cggtggtggt   420
ggtagcggta tgcaggttca gctgcagcag agcggtgcag aactggttaa accgggtaca   480
agcgttaaac tgagctgtaa agcaagcggt tatacctta cccgcaatca tatgaattgg   540
gtgaaacaga ccaccggtca gggtctggaa tggattggtc gtattaatcc gggtacaggt   600
ggcaccagct ataatgtgaa ttttaaaggc aaagcaaccc tgaccgttga tgaaagcagc   660
agcaccgcat ttatgcagct gagcagcctg acaccggaag atagcgcagt gtactactgt   720
gcacgtggcg atagctattg gtattttgat ttttggggtc cgggtacaat ggttaccgtt   780
agcggtagcg gtggtggcgg ttctggtggt ggtggctcag gtggcggtgg ttctgatgtt   840
cagatgaccc agagcccgta atctggttgc atctccgg gtgaaagcgt tagcattaat   900
tgcaaagcca gcaaaagcat tagcaaatat ctggcatggt atcagcagaa accgggtaaa   960
gcaaataaac tgctgattta tgaaggtagc accctgcaga gcggtattcc gagccgtttt  1020
agcggttctg gtagcggcac cgattttacc ctgaccattc gtagcctgga accggaagat  1080
tttggtctgt attattgcca gcagcataat gaatatccgc tgacctttgg tagcggtaca  1140
aaactggaaa ttaaacgtgc agatgcagca ccgaccgttg cagcagctcc gcgtggtggt  1200
ccggaacaga aactgattag cgaagaagat ctgaatagcg cagttgatc              1249
```

<210> SEQ ID NO 21
<211> LENGTH: 424
<212> TYPE: PRT
<213> ORGANISM: artificial
<220> FEATURE:
<223> OTHER INFORMATION: antibody construct

<400> SEQUENCE: 21

```
Met Gly Ser Gln Val Gln Leu Gln Glu Ser Gly Gly Gly Leu Val Gln
1               5                   10                  15

Pro Gly Gly Ser Leu Arg Leu Ser Cys Ala Ala Ser Gly Arg Thr Phe
            20                  25                  30

Ser Asp His Ser Gly Tyr Thr Tyr Thr Ile Gly Trp Phe Arg Gln Ala
        35                  40                  45

Pro Gly Lys Glu Arg Glu Phe Val Ala Arg Ile Tyr Trp Ser Ser Gly
    50                  55                  60

Asn Thr Tyr Tyr Ala Asp Ser Val Lys Gly Arg Phe Ala Ile Ser Arg
65                  70                  75                  80

Asp Ile Ala Lys Asn Thr Val Asp Leu Thr Met Asn Asn Leu Glu Pro
            85                  90                  95

Glu Asp Thr Ala Val Tyr Tyr Cys Ala Ala Arg Asp Gly Ile Pro Thr
            100                 105                 110

Ser Arg Ser Val Glu Ser Tyr Asn Tyr Trp Gly Gln Gly Thr Gln Val
            115                 120                 125

Thr Val Ser Ser Ala Gly Ala Gly Ser Gly Gly Gly Ser Gly Met
            130                 135                 140

Gln Val Gln Leu Gln Gln Ser Gly Ala Glu Leu Val Lys Pro Gly Thr
145                 150                 155                 160

Ser Val Lys Leu Ser Cys Lys Ala Ser Gly Tyr Thr Phe Thr Arg Asn
            165                 170                 175

His Met Asn Trp Val Lys Gln Thr Thr Gly Gln Gly Leu Glu Trp Ile
            180                 185                 190

Gly Arg Ile Asn Pro Gly Thr Gly Gly Thr Ser Tyr Asn Val Asn Phe
            195                 200                 205

Lys Gly Lys Ala Thr Leu Thr Val Asp Glu Ser Ser Ser Thr Ala Phe
210                 215                 220

Met Gln Leu Ser Ser Leu Thr Pro Glu Asp Ser Ala Val Tyr Tyr Cys
225                 230                 235                 240

Ala Arg Gly Asp Ser Tyr Trp Tyr Phe Asp Phe Trp Gly Pro Gly Thr
            245                 250                 255

Met Val Thr Val Ser Gly Ser Gly Gly Gly Ser Gly Gly Gly Gly
            260                 265                 270

Ser Gly Gly Gly Gly Ser Asp Val Gln Met Thr Gln Ser Pro Tyr Asn
            275                 280                 285

Leu Val Ala Ser Pro Gly Glu Ser Val Ser Ile Asn Cys Lys Ala Ser
            290                 295                 300

Lys Ser Ile Ser Lys Tyr Leu Ala Trp Tyr Gln Gln Lys Pro Gly Lys
305                 310                 315                 320

Ala Asn Lys Leu Leu Ile Tyr Glu Gly Ser Thr Leu Gln Ser Gly Ile
            325                 330                 335

Pro Ser Arg Phe Ser Gly Ser Gly Ser Gly Thr Asp Phe Thr Leu Thr
            340                 345                 350

Ile Arg Ser Leu Glu Pro Glu Asp Phe Gly Leu Tyr Tyr Cys Gln Gln
            355                 360                 365

His Asn Glu Tyr Pro Leu Thr Phe Gly Ser Gly Thr Lys Leu Glu Ile
            370                 375                 380

Lys Arg Ala Asp Ala Ala Pro Thr Val Ala Ala Pro Arg Gly Gly
385                 390                 395                 400

Pro Glu Gln Lys Leu Ile Ser Glu Glu Asp Leu Asn Ser Ala Val Asp
            405                 410                 415

Leu Glu His His His His His His
```

<210> SEQ ID NO 22
<211> LENGTH: 424
<212> TYPE: PRT
<213> ORGANISM: artificial
<220> FEATURE:
<223> OTHER INFORMATION: antibody construct

<400> SEQUENCE: 22

```
Met Gly Ser Gln Val Gln Leu Gln Glu Ser Gly Gly Gly Leu Val Gln
1               5                   10                  15
Pro Gly Gly Ser Leu Arg Leu Ser Cys Ala Ala Ser Gly Arg Thr Phe
            20                  25                  30
Ser Asp His Ser Gly Tyr Thr Tyr Thr Ile Gly Trp Phe Arg Gln Ala
        35                  40                  45
Pro Gly Lys Glu Arg Glu Phe Val Ala Arg Ile Tyr Trp Ser Ser Gly
    50                  55                  60
Asn Thr Tyr Tyr Ala Asp Ser Val Lys Gly Arg Phe Ala Ile Ser Arg
65                  70                  75                  80
Asp Ile Ala Lys Asn Thr Val Asp Leu Thr Met Asn Asn Leu Glu Pro
                85                  90                  95
Glu Asp Thr Ala Val Tyr Tyr Cys Ala Ala Arg Asp Gly Ile Pro Thr
            100                 105                 110
Ser Arg Ser Val Glu Ser Tyr Asn Tyr Trp Gly Gln Gly Thr Gln Val
        115                 120                 125
Thr Val Ser Ser Ala Gly Ala Gly Ser Gly Gly Gly Ser Gly Met
    130                 135                 140
Gln Val Gln Leu Gln Gln Ser Gly Ala Glu Leu Val Lys Pro Gly Thr
145                 150                 155                 160
Ser Val Lys Leu Ser Cys Lys Ala Ser Gly Gly Gly Ser Gly Gly
                165                 170                 175
Gly Gly Ser Trp Val Lys Gln Thr Thr Gly Gln Gly Leu Glu Trp Ile
            180                 185                 190
Gly Gly Gly Gly Gly Gly Ser Gly Gly Gly Gly Ser Gly Gly Gly Gly
        195                 200                 205
Gly Ser Lys Ala Thr Leu Thr Val Asp Glu Ser Ser Thr Ala Phe
    210                 215                 220
Met Gln Leu Ser Ser Leu Thr Pro Glu Asp Ser Ala Val Tyr Tyr Cys
225                 230                 235                 240
Ala Arg Gly Gly Gly Ser Gly Gly Gly Ser Trp Gly Pro Gly Thr
                245                 250                 255
Met Val Thr Val Ser Gly Ser Gly Gly Gly Ser Gly Gly Gly Gly
            260                 265                 270
Ser Gly Gly Gly Gly Ser Asp Val Gln Met Thr Gln Ser Pro Tyr Asn
        275                 280                 285
Leu Val Ala Ser Pro Gly Glu Ser Val Ser Ile Asn Cys Gly Gly Gly
    290                 295                 300
Gly Ser Gly Gly Gly Gly Ser Gly Trp Tyr Gln Gln Lys Pro Gly Lys
305                 310                 315                 320
Ala Asn Lys Leu Leu Ile Tyr Gly Ser Gly Gly Ser Gly Gly Ile
                325                 330                 335
Pro Ser Arg Phe Ser Gly Ser Gly Ser Gly Thr Asp Phe Thr Leu Thr
            340                 345                 350
Ile Arg Ser Leu Glu Pro Glu Asp Phe Gly Leu Tyr Tyr Cys Gly Gly
```

-continued

```
            355                 360                 365
Gly Ser Gly Gly Gly Gly Ser Phe Gly Ser Gly Thr Lys Leu Glu Ile
        370                 375                 380

Lys Arg Ala Asp Ala Ala Pro Thr Val Ala Ala Ala Pro Arg Gly Gly
385                 390                 395                 400

Pro Glu Gln Lys Leu Ile Ser Glu Glu Asp Leu Asn Ser Ala Val Asp
                405                 410                 415

Leu Glu His His His His His His
                420
```

BI-SPECIFIC AFFINITY REAGENTS FOR CELL-LINEAGE-SPECIFIC TNF-ALPHA NEUTRALIZATION

CROSS-REFERENCE TO RELATED APPLICATIONS

This is the U.S. national stage of International application PCT/EP2013/072470, filed Oct. 28, 2013 designating the United States and claiming priority to European Application EP 12190112.8, filed Oct. 26, 2012.

INCORPORATION OF SEQUENCE LISTING

The sequence listing was filed as a text file as part of International application PCT/EP2013/072470, on May 1, 2014 is hereby incorporated by reference. An extra copy of this text file named "eolf-seql.txt", which is 21 kilobytes (measured in MS-WINDOWS), dated Apr. 24, 2015 was downloaded from WIPO and is submitted herewith via the USPTO EFS system.

The invention relates to isolated bispecific affinity reagents, such as antibodies or antibody fragments that bind TNFα and a marker molecule for macrophages and/or neutrophils. The affinity reagents of the invention enable predominantly pathogenic sub-populations of TNFα to be neutralised, whilst protective sub-populations of TNFα are not affected.

The bi-specific affinity reagents preferably bind specifically to macrophage cells, responsible for pathogenic TNFα production, in addition to TNFα itself. The bi-specific affinity reagents preferably do not bind protective TNFα produced in other cells types, such as T cells, or bind TNFα produced in other cell types only to a reduced extent in comparison to a pan-TNFα blockade approach, for example as shown by a mono-specific antibody against TNFα.

Tumour necrosis factor alpha (referred to as TNF, TNF-alpha, TNFα) is an immunomodulatory and pro-inflammatory cytokine produced by many types of immunocytes and targets a wide spectrum of cells and tissues. Its local or systemic overproduction may be deleterious and result in disease states, and, conversely, several autoimmune diseases with an inflammatory component can be ameliorated by a TNF blockade. The present invention shows that in light of the complex pattern of TNF production and the range of its physiological effects, the source and molecular form of TNF is associated with distinct protective or pathological functions. The "pan-TNF" blockade, which is currently used to treat rheumatoid arthritis (RA) and several other diseases, will be further improved if only pathogenic TNF sources are blocked while protective TNF production is minimally disturbed. For example complete ablation of TNF results in some cases in the loss of critical protective functions against pathogenic infection.

The present invention relates therefore to the selective blockade of TNF on the cellular sources of pathogenic versions of the cytokine, for example TNF on macrophages or neutrophils, and its comparable efficacy, as shown in an example in ameliorating experimental arthritis in mice. It however only minimally interferes with the integrity of protective granulomas in protective responses against bacterial infections. The invention uses murine models and prototype reagents to demonstrate the efficacy of this approach. The invention therefore provides new avenues in the anti-cytokine therapy of various diseases.

BACKGROUND OF THE INVENTION

TNF is involved in pathogenesis of several autoimmune diseases with an inflammatory component and TNF blockers can be very effective for the therapy of rheumatoid arthritis (RA). Over 2 million RA patients have been treated with such drugs worldwide. However, this treatment is not curative since disease usually relapses after interruption of therapy. The standard treatment also interferes with protective functions of TNF against bacterial or other pathogenic infections.

TNF inhibition puts patients at increased risk of opportunistic infections. Warnings have been issued about the risk of infection from two bacterial pathogens, in particular *Legionella* and *Listeria*. People taking TNF blockers are at increased risk for developing serious infections that may lead to hospitalization or death due to bacterial, mycobacterial, fungal, viral, parasitic, and other opportunistic pathogens. Tuberculosis represents a major risk for patients undergoing anti-TNF treatment. In patients with latent *Mycobacterium tuberculosis* infection, active tuberculosis (TB) may develop soon after the initiation of treatment with infliximab (a known anti-TNF medicament). Before prescribing the drug, physicians should screen patients for latent or chronic TB infection or disease. In some cases, even latent infection screening does not provide suitable or sufficient identification of patients at risk of infections enabled by pan anti-TNF treatments (Jauregui-Amezaga et al., J Crohns Colitis. 2013 Apr. 1; 7(3):208-12).

The anti-TNF monoclonal antibody biologics, such as Infliximab and adalimumab, and the fusion protein etanercept which are all currently approved by the U.S. Food and Drug Administration (FDA) for human use, have warnings which state that patients should be evaluated for latent or chronic TB infection and treatment should be initiated prior to starting therapy with these medications. Additional warnings have been issued that patients on TNF inhibitors are at increased risk of opportunistic fungal infections, such as pulmonary and disseminated histoplasmosis, coccidioidomycosis, and blastomycosis.

Cytokines associated with inflammation and inflammation-related medical disorders, such as TNF-alpha, show both protective and pathological functions, which represents a significant drawback in anti-cytokine therapy. The cell-lineage specific blockade or neutralisation of such cytokines is therefore an important possibility in addressing the different functions of any given cytokine.

The present invention therefore utilises blocking the principal cellular sources of pathogenic TNF in arthritis, and shows how a specific TNF blockade may lead to amelioration of disease symptoms without reduced risks of detrimental side effects due to unwanted neutralisation of protective TNF.

The idea that distinct cellular sources of TNF and its main two molecular forms (secreted and membrane bound) can be distinctly associated with various TNF functions in healthy mice is consistent with a recent study (Tumanov et al. 2010) concerning homeostatic role of TNF in lymphoid tissues, as well as with an earlier work (Grivennikov et al. 2005). It was however unknown in the art that the same is true for the role of TNF in disease: that some cellular sources of TNF may be pathogenic, while others are neutral or protective. The data provided herein demonstrate separate physiological roles in disease for TNF produced by different cellular sub-populations, although a mechanistic explanation of why macrophage TNF is pathogenic in experimental arthritis, while TNF produced by T cells appears protective, is still somewhat unclear.

Using collagen-induced arthritis (CIA) as an animal model for RA, the inventors and others have found that arthritogenic T cells accumulate in large numbers in lymphoid organs of TNF-deficient mice or of wild-type mice treated with TNF blockers, despite the resistance of these mice to disease induction (Notley et al. 2008). Therefore, a pan-TNF blockade may reduce the manifestation of arthritis (possibly by suppressing the infiltration of immune cells into joints), while concomitantly disrupting mechanisms of immune regulation thereby leading to accumulation of pathogenic cells in other body locations. Another possibility is the action of TNF blockers on organized structures of lymphoid tissues, in particular, germinal centers, and related effects on B cell compartment, including B cell memory (Anolik et al. 2008).

Various antibodies directed to TNFα are known in the art. For example WO 2008/003116 A2 discloses a method for engineering an immunoglobulin, in particular for engineering bi-specific antibodies, for an anti-TNF-alpha treatment.

Bi-specific affinity reagents that bind TNFα and an additional marker have been described in the art. WO 2006/063150 A2 discloses methods and reagents for immunotherapy of inflammatory diseases using multi-specific antagonists such as bispecific antibodies that target at least two different markers. Different targets include proinflammatory effectors of the immune system or particular cell types involved in immune responses. The use of an anti-TNF-alpha/anti-CD83 bispecific antibody, which may bind dendritic cells, is disclosed for the treatment of Systemic Lupus Erythematosus (SLE). No details are disclosed regarding a bi-specific affinity reagent directed towards TNFα and a macrophage or neutrophils marker. Furthermore, the concept of differential neutralisation of pathogenic and protective TNFα sub-populations is not disclosed.

Kanakaraj Palanisamy et al (MAbs. 2012 Sep. 1; 4(5): 600-613) disclose a bispecific antibody targeted to TNF-alpha and Ang2 for the treatment of arthritis. According to this publication the combination of anti-TNF-alpha and anti-angiogenic agents may control inflammation more effectively, if angiogenesis initiates chronic inflammation. No details are disclosed regarding a bi-specific affinity reagent directed towards TNFα and a marker for macrophages or neutrophils and the concept of differential neutralisation of pathogenic and protective TNFα sub-populations is not mentioned.

SUMMARY OF THE INVENTION

In light of the prior art the technical problem underlying the invention was the provision of further or improved agents for TNFα neutralisation that do not exhibit the disadvantages of those agents known in the art. In particular, reagents are sought that enable the benefits of anti-TNFα therapy but do not impinge on important protective functions of TNFα.

This problem is solved by the features of the independent claims. Preferred embodiments of the present invention are provided by the dependent claims.

Therefore, an object of the invention is to provide an isolated bispecific affinity reagent, such as an antibody or antibody fragment, that predominantly binds and/or neutralises TNFα produced in macrophages and/or neutrophils compared to TNFα produced in other cell types, wherein the bispecific antibody or antibody fragment comprises one or more amino acid sequences that specifically bind TNFα and a marker molecule for macrophages and/or neutrophils.

This approach provides neutralisation of pathogenic cytokine in a specific or nearly specific manner leaving protective cytokine from other cellular sources to a large extent undisturbed. To the knowledge of the inventors, the present invention represents the first application of a bispecific antibody, which binds both a cell-lineage specific marker and a cytokine, in order to neutralise pathogenic cytokine in a cell-lineage specific manner. It was entirely surprising, that the antibodies as described herein would exhibit the desired properties of bi-specificity and therefore neutralise only (or predominantly) the pathogenic form of TNFα. It was also a novel and unexpected finding that a cytokine population, which exhibits both pathogenic and protective functions, can be selectively and specifically neutralised, wherein essentially only (or predominantly) the pathogenic form of the cytokine is neutralised, by targeting the cytokine according to the cell-lineage or cell-type in which the cytokine was produced. The phrase "predominantly" refers to increased binding of TNFα produced in macrophages and/or neutrophils compared to TNFα produced in other cell types, or in other embodiments, to more pronounced binding to the TNF produced in macrophages or neutrophils in comparison to binding by a mono-specific antibody directed to TNF alpha.

The present invention is particularly relevant for the treatment of inflammatory diseases caused or associated with TNF expression. Diseases associated with inflammation are known to a skilled person, whereby inflammation itself represents a clear indicator of a medical disorder to be treated. Preferred diseases are for example rheumatoid arthritis, MS or other inflammatory autoimmune disease. The preferred disorders listed herein are not intended to limit the scope of the invention.

The invention therefore relates to an isolated bi-specific antibody or antibody fragment as described herein, characterised in that TNFα produced in cell types other than macrophages and neutrophils is not bound and/or neutralised, or bound and/or neutralised to a reduced extent in comparison to a monospecific TNFα antibody or antibody fragment. In one embodiment the isolated bispecific antibody or antibody fragment of the invention is characterised in that TNFα produced in T cells is not bound and/or neutralised, or bound and/or neutralised to a reduced extent in comparison to a monospecific TNFα antibody or antibody fragment. This characterising feature relates to a novel technical effect that has been neither described nor suggested in the context of a bispecific affinity reagent capable of providing cell-lineage specific binding as described herein.

One important aspect of the invention relates to the novel and inventive recognition that cell-source-specific TNF neutralisation via an affinity reagent enables cytokine therapy with reduced side effects, in particular anti-TNF treatments with reduced risk of activation of TB infection in cases of latent or chronic infection. As described above, recurring TB activation in patients with latent infection is one of the most significant side effects of pan-TNF treatment regimes. Because both pathogenic and protective TNF is neutralised, the patient is left susceptible to infection by any given infectious disease, in particular reactivation of already existing TB.

The predominant selective neutralisation of pathogenic TNF (i.e. TNF alpha produced in macrophages and/or neutrophils) via the administration of a bispecific affinity reagent, in particular an antibody or antibody fragment or combination thereof, represents a novel technical effect, which has been described previously in the art. This novel technical effect enables a new clinical situation in light of the existing prior art. The technical effect of selective neutralisation of pathogenic TNF via a bispecific antibody directed towards a cell-type-specific marker enables the treatment of groups of patients, previously thought to have been untreatable (or only treatable at high risk) with existing TNF therapies.

Those patients susceptible of pathogenic infection, in particular TB activation in cases of latent infection, could not be safely treated for inflammatory disease, for example arthritis, due to the risk of infection, due to the reduced protective function of TNF after anti-TNF treatment. The present invention enables treatment of these groups due to the technical effect described and demonstrated herein, namely anti-inflammatory treatment via anti-TNF without depletion of TNF with protective function, for example TNF produced from T cells.

As has been shown experimentally, TNF is critical for host control of *M. tuberculosis*, but the relative contribution of TNF from innate and adaptive immune responses during tuberculosis infection is unclear. Myeloid (such as macrophage/neutrophil) versus T-cell-derived TNF function in tuberculosis was investigated using cell type-specific TNF deletion. Mice deficient for TNF expression in macrophages/neutrophils displayed early, transient susceptibility to *M. tuberculosis* but recruited activated, TNF-producing CD41 and CD81 T-cells and controlled chronic infection.

Deficient TNF expression in T-cells however resulted in early control but susceptibility and eventual mortality during chronic infection with increased pulmonary pathology. TNF inactivation in both myeloid and T-cells rendered mice critically susceptible to infection with a phenotype resembling complete TNF deficient mice, indicating that myeloid and T-cells are the primary TNF sources collaborating for host control of tuberculosis. Thus, while TNF from myeloid cells mediates early immune function (and this source is probably redundant), T-cell derived TNF is essential to sustain protection during chronic tuberculosis infection.

In light of these findings, the selective (predominant) neutralisation of TNF produced from macrophages, without affecting TNF produced by T cells, enables host control of *M. tuberculosis* in chronic and latent infection. Considering the reactivation of TB is one of the most significant side effects/risk of TNF therapy, the present invention represents a significant step forward in enabling the treatment of patients with latent TB infections, or patients at risk of other infectious diseases. Even though a minimal risk of acute infection may remain due to macrophage-selected neutralization of TNF, this scenario represents an enormous improvement over standard mono-specific anti-TNF antibodies, which also deplete protective TNF.

The antibody or antibody fragment of the invention also enables significantly lower doses during administration compared to the pan TNF antibodies presently used in the art. Because a substantial amount of antibody is required during traditional anti-TNF-alpha treatment—post-administration, in vivo—to bind to all TNF in the patient (including TNF which should not be targeted i.e. protective TNF), more (higher concentrations of) mono-specific antibody must be administered during traditional treatment in order to achieve the same TNF neutralisation effect. This subsequently leads to other side effects that occur in combination with the administration of high concentrations of antibodies, such as headache, fever, chills, nausea, heartburn, flushing, weakness, or dizziness. In comparison, the present invention provides a selective and targeted solution to anti-TNF-alpha treatment, targeting only pathogenic TNF-alpha and thereby requiring the binding and neutralisation of subset of all TNF, thereby requiring lower levels of antibody to be administered, thereby reducing general side effects and/or risks thereof.

The marker molecule for macrophages and/or neutrophils relates preferably to a protein, or other biological molecule, that is present preferably on the surface of macrophages or neutrophils. The concept of cell-type specific markers is known in the art. In one embodiment the marker molecule for macrophages and/or neutrophils is expressed specifically in these cell types. Such a molecule may be, in one embodiment, a protein that is expressed, or is present, specifically in macrophages and/or neutrophils, and which is preferably to be found on the surface of these cell types. The phrase “specifically” is intended to relate to molecular markers, such as proteins, that are found predominantly on certain cell types. Such molecules may be expressed at low levels on other cell types or cell lineages. If the marker molecule of interest is expressed predominantly in macrophages and/or neutrophils, in comparison to other cell types, the marker molecule may, in one embodiment, be considered a marker molecule for macrophages and/or neutrophils.

In a preferred embodiment the invention relates to an isolated bispecific antibody or antibody fragment as described herein, characterised in that the marker molecule for macrophages and/or neutrophils is F4/80 (EMR1), CD163, CD169 or Mer TK (Camenisch et al. Journal of Immunology, 1999, Mar. 15; 162(6):3498-503; Scott et al, Nature 2001, May 10; 411(6834):207-11). Various markers for macrophages and/or neutrophils are known in the art. In one embodiment the invention is not limited to any single marker molecule but is characterised preferably by a binding specificity of the bispecific affinity reagent to the cell types macrophages and/or neutrophils as described herein.

EMR1 is the human protein for F4/80 and is functionally analogous to its mouse counterpart. CD163 is the human scavenger receptor specific for monocyte/macrophage lineage. CD169 is sialoadhesion that belongs to the Siglec family and is a marker for macrophages. Mer Tk is a receptor with tyrosine kinase activity involved in recognition of apoptotic cells by macrophages.

All protein or gene names mentioned herein originating from the mouse are intended to encompass the human homologues or functional analogues, which are disclosed herein by reference to the mouse gene or protein. The treatment of a human subject falls under the scope of the present invention, therefore the human analogues to the mouse proteins and/or genes are also encompassed by the invention and inherently disclosed herein. The identification of a human homologues or functional analogue of a mouse molecule described herein requires no inventive effort for a skilled person.

The various marker molecules for macrophages and/or neutrophils provided herein are bound by a novel and unitary special technical feature in the context of the bispecific antibody described herein. The combination between a binding domain specific for any given marker molecule for macrophages and/or neutrophils and a TNF-specific binding domain, provided in order to enable selective neutralisation of a pathogenic sub-population of TNF, represents a special technical feature common to all possible marker molecules for macrophage and/or neutrophils.

Specific embodiments for F4/80 and TNF-$\alpha$-binding antibodies are provided below. It is however encompassed in the scope of the invention that antibodies or antibody fragments that bind F4/80, EMR1, CD163, CD169 or Mer Tk, may be used in designing the bispecific antibodies of the invention. In light of this contribution to the art, known sequences may be used in the bispecific antibodies of the present invention, although the provision of specific sequences may also be seen as an inventive contribution to the art.

In one embodiment of the invention the isolated bispecific antibody or antibody fragment is characterised in that it is a chimeric, humanised or single chain antibody or single domain antibody (VHH), or combination thereof. Methods of creating chimeric or humanised antibodies are known in the art. Common approaches towards sequence improvements, although technically difficult, which reduce side effects in human patients but retain specific binding, are known in the art, so that these variants of antibodies are included in the scope of the present invention.

In a preferred embodiment of the invention the isolated bispecific antibody or antibody fragment is characterised in that it comprises one or more TNFα binding domains, and F4/80 (EMR1) binding domains. This particular combination is shown to function via multiple experimental examples shown below. The neutralisation of TNF-alpha (TNFα) that is produced from macrophages is a preferred target of the present invention. Bispecific antibodies directed to other macrophage or neutrophil markers are also considered to fall within the scope of the invention.

The following embodiments represent specific antibodies that are known to exhibit the desired properties of the invention. The specific sequences are provided as examples and are not intended to limit the scope of the invention. Importantly, when the specificity (target selectivity) of the antibody is known, various further antibody or other affinity reagent sequences can be generated in a routine and non-inventive manner in order to generate further affinity reagents with said specificity.

Via immunisation with antigens in mice (or other mammals), subsequent isolation of antibody producing spleen cells, fusion to form hybridoma cells and subsequent culture and selection for specifically binding antibodies, monoclonal antibodies may be produced with alternative sequences but analogous binding specificities as those antibodies explicitly described herein. Polyclonal antibodies with said specific binding properties may also be obtained via known methods, such as immunisation with antigens in rabbits, and subsequent selection of antibodies from the rabbit (or other mammal) that bind the desired epitopes. Various sequences can be obtained against any given antigen without undue effort for a skilled person. This enables therefore further amino acid sequences for antibodies with the same desired binding specificities as those explicitly disclosed herein.

For example, the proteins F4/80 (EMR1), CD163, CD169 or Mer TK, or fragments thereof, preferably protein fragments presented on the cell surface of macrophages or neutrophils, may be used as antigens to immunise mice or other mammals in order to produce antibodies against said antigens. The respective binding regions can be subsequently cloned from the antibodies produced by such methods to engineer further antibodies with the desired specificity.

In one embodiment of the invention the isolated bispecific antibody or antibody fragment is characterised in that the TNFα binding domain is a single-domain antibody, preferably a VHH domain, preferably isolated from Camelids and further engineered for higher binding affinity, preferably comprising

- a sequence according to SEQ ID No. 1 (MGSQVQLQESGGGLVQPGGSLRLSCAASGRTFSDHSGYTYTIGWFRQAPGK EREFVARIYWSSGNTYYADSVKGRFAISRDIAKNTVDLTMNNLEPEDTAVYYCA ARDGIPTSRSVESYNYWGQGTQVTVSSAGA), or
- a sequence with TNFα binding properties and a sequence identity to SEQ ID No. 1 of at least 80%, preferably 90%, more preferably 95%.

It was surprising, that the VHH domain described herein exhibited good specificity and binding in assays conducted for TNF-alpha binding in the context of a bi-specific reagent. The sequence provided herein also showed good stability under various storage conditions in addition to in vivo half-life.

In one embodiment of the invention the isolated bispecific antibody or antibody fragment is characterised in that the anti-F4/80 and/or anti-EMR1 binding domain comprises a single chain variable fragment (scFv), preferably comprising

- a VH domain comprising at least one CDR region selected from CDR H1 (SEQ ID No. 2: GYTFTNHMN), CDR H2 (SEQ ID No. 3: RINPGTGGTSYNVNFKG) and CDR H3 (SEQ ID No. 4: GDSYWYFDF),
- a VH domain comprising at least one CDR region selected from a sequence with a sequence identity to SEQ ID No. 2, 3 or 4 of at least 80%, preferably 90%, more preferably 95%,
- a VL domain comprising at least one CDR region selected from CDR L1 (SEQ ID No. 5: KASKSISKYLA), CDR L2 (SEQ ID No. 6: EGSTLQS) and CDR L3 (SEQ ID No. 7: QQHNEYPLT), and/or
- a VL domain comprising at least one CDR region selected from a sequence with a sequence identity to SEQ ID No. 5, 6 or 7 of at least 80%, preferably 90%, more preferably 95%.

In one embodiment of the invention the isolated bispecific antibody or antibody fragment is characterised in that it comprises

- a VH domain comprising a sequence according to SEQ ID No. 8 (MQVQLQQSGAELVKPGTSVKLSCKASGYTFTNHMNWVKQTTGQGLEWIGRI NPGTGGTSYNVNFKGKATLTVDESSSTAFMQLSSLTPEDSAVYYCARGDSYW YFDFWGPGTMVTVSGS) or a sequence with a sequence identity to SEQ ID No. 8 of at least 80%, preferably 90%, more preferably 95%,
- a VL domain comprising a sequence according to SEQ ID No. 9 (DVQMTQSPYNLVASPGESVSINCKASKSISKYLAWYQQKPGKANKLLIYEGST LQSGIPSRFSGSGSGTDFTLTIRSLEPEDFGLYYCQQHNEYPLTFGSGTKLEIK RADAAPTVAAAPRGGPEQKLISEEDLNSAVD) or a sequence with a sequence identity to SEQ ID No. 9 of at least 80%, preferably 90%, more preferably 95%, and/or
- a sequence according to SEQ ID 10 or 21 or a sequence with TNFα and myeloid cell binding properties and a sequence identity to SEQ ID No. 10 or 21 of at least 80%, preferably 90%, more preferably 95%.

In one embodiment the invention relates to an antibody or antibody fragment that comprises VH and VL domain sequences with a sequence identity of at least 80%, preferably 90%, more preferably 95%, to SEQ ID No. 8 and/or 9, respectively, and comprises CDR regions CDR H1 (SEQ ID No. 2: GYTFTNHMN), CDR H2 (SEQ ID No. 3: RINPGTGGTSYNVNFKG), CDR H3 (SEQ ID No. 4: GDSYWYFDF), CDR L1 (SEQ ID No. 5: KASKSISKYLA), CDR L2 (SEQ ID No. 6: EGSTLQS) and CDR L3 (SEQ ID No. 7: QQHNEYPLT).

It was surprising, that the anti-F4/80 (or anti-EMR1) binding domain, comprising a single chain variable fragment (scFv) as described herein, exhibited good specificity and binding in assays conducted for F4/80-binding. The sequence provided herein also showed surprisingly good stability under various storage conditions in addition to extended in vivo half-life.

In a preferred embodiment of the invention the isolated bispecific antibody or antibody fragment is characterised in that it binds and neutralises TNFα produced in myeloid cells, preferably macrophages, without, or with a reduced extent of, neutralisation of TNFα produced in other cell types. This embodiment represents one of the significant advantageous properties of the antibodies described herein. Through the bispecificity the antibodies neutralise only those TNF-alpha molecules (or at least a significant amount of such molecules in comparison to TNF-alpha from other cellular sources) from the source defined by the specificity of the lineage-specific marker portion of the antibody. This leads to minimisation of unwanted side effects of pan-TNF blockades, such as reduced immunity of the patient against pathogens.

A further aspect of the invention is an isolated bispecific antibody or antibody fragment as described herein, whereby patients receiving treatment exhibit a reduced risk of infection, for example from bacterial, viral or fungal infections, in comparison to patients undergoing treatment with cell-type-unspecific anti-TNFα therapy. This embodiment is a particularly beneficial aspect of the invention, allowing maintenance of a functioning immune system, via maintaining protective TNF-alpha function, while also providing treatment of any given inflammatory condition.

A further aspect of the invention relates to the isolated bispecific antibody or antibody fragment as disclosed herein for use as a medicament in the treatment of a medical disorder associated with inflammation, preferably rheumatic disorder or auto immune disease with an inflammatory component. A method of treatment of said disorders is also therefore encompassed, in which a therapeutically effective amount of antibody is administered to a subject in need of treatment, suffering from said condition(s).

A further aspect of the invention relates to a preferably isolated nucleic acid molecule selected from the group comprising:
a) a nucleic acid molecule comprising a nucleotide sequence which encodes an isolated bispecific antibody or antibody fragment according to any one of the preceding claims or an amino acid sequence selected from the group consisting of SEQ ID No. 1, 2, 3, 4, 5, 6, 7, 8, 9, 10 or 21,
preferably comprising a sequence according to SEQ ID No. 11, 12, 13, 14, 15, 16, 17, 18, 18, or 20;
b) a nucleic acid molecule which is complementary to a nucleotide sequence in accordance with a);
c) a nucleic acid molecule comprising a nucleotide sequence having sufficient sequence identity to be functionally analogous/equivalent to a nucleotide sequence according to a) or b), comprising preferably a sequence identity to a nucleotide sequence according to a) or b) of at least 80%, preferably 90%, more preferably 95%;
d) a nucleic acid molecule which, as a consequence of the genetic code, is degenerated into a nucleotide sequence according to a) through c); and
e) a nucleic acid molecule according to a nucleotide sequence of a) through d) which is modified by deletions, additions, substitutions, translocations, inversions and/or insertions and functionally analogous/equivalent to a nucleotide sequence according to a) through d).

In one embodiment the nucleic acid molecule as described herein is characterized in that it is a genomic DNA, a cDNA and/or RNA. A vector, such as an expression vector, comprising a nucleic acid molecule as described herein is also encompassed within the invention. For example, a promoter region would be operably linked to a DNA sequence if the promoter were capable of effecting transcription of that DNA sequence. The nucleic acid segment encoding the antibody or variant of the invention or a N-terminal fragment thereof or a C-terminal fragment thereof should thus be linked to regulatory elements, such as a promoter and enhancer, which allows expression of the nucleic acid segment in the intended host.

A further aspect of the invention relates to a host cell, such as a bacterial cell or mammalian cell, preferably a hybridoma cell or cell line, capable of producing a bispecific antibody or antibody fragment as described herein, and/or comprising a nucleic acid molecule as described herein.

A further aspect of the invention relates to a pharmaceutical composition comprising the isolated bispecific antibody or antibody fragment as described herein, a nucleic acid molecule or a host cell as described herein, together with a pharmaceutically acceptable carrier.

DETAILED DESCRIPTION OF THE INVENTION

In the context of the present invention the term "bi-specific" relates to the capability of an antibody or antibody fragment to bind two antigens in a specific manner. In the present invention the term "multi-specific" could also be used. "Specific binding" is to be understood as via one skilled in the art, whereby the skilled person is clearly aware of various experimental procedures that can be used to test binding and binding specificity. Some cross-reaction or background binding may be inevitable in many protein-protein interactions; this is not to detract from the "specificity" of the binding between antibody and epitope. The term "directed against" is also applicable when considering the term "specificity" in understanding the interaction between antibody and epitope.

The term cell-type or cell-lineage may be used interchangeably and indicate the identity of the cell in the subject to be targeted by the antibody. Examples for cell-types and/or cell-lineages are provided herein. Cytokines as such are known to a skilled person. Cytokines are small cell-signalling protein molecules that are secreted by numerous cells and are a category of signalling molecules used extensively in intercellular communication. Preferred molecules under the term "cytokine" are immunomodulating agents, such as TNF, interleukins and interferons.

Macrophages, sometimes called macrophagocytes, are cells produced by the differentiation of monocytes in tissues and are a predominant source of TNF-alpha. Macrophages are phagocytes and function in both non-specific defense (innate immunity) as well as help initiate specific defense mechanisms (adaptive immunity) of vertebrate animals. They also stimulate lymphocytes and other immune cells to respond to pathogens. Macrophages represent specialized phagocytic cells that attack foreign substances, infectious microbes and cancer cells through destruction and ingestion. Macrophages can be identified by specific expression of a number of proteins including F4/80 (EMR1), CD163, CD169 or Mer TK, CD14, CD40, CD11 b, CD64, lysozyme M, MAC-1/MAC-3 and CD68 by flow cytometry or immunohistochemical staining or other corresponding techniques. Such markers may be used as targets of the affinity reagent of the present invention.

Neutrophil granulocytes (also known as neutrophils or polymorphonuclear leukocytes (PMNs)) are an abundant type of white blood cell in mammals and form an essential part of the innate immune system and express TNF. Neutrophils may be subdivided into segmented neutrophils (or segs) and banded neutrophils (or bands). They form part of the polymorphonuclear cell family (PMNs) together with basophils and eosinophils. Neutrophils may be characterised by staining characteristics on hematoxylin and eosin (H&E) histological or cytological preparations.

Whereas basophilic white blood cells stain dark blue and eosinophilic white blood cells stain bright red, neutrophils stain a neutral pink. Neutrophils are a type of phagocyte and are normally found in the blood stream. During the beginning (acute) phase of inflammation, particularly as a result of bacterial infection, environmental exposure and some cancers, neutrophils are one of the first-responders of inflammatory cells to migrate towards the site of inflammation. Neutrophils may be identified by expression of a number of proteins including neutrophil CD64, Gelatinase Granulocyte Receptor-1 (Gr-1), HNL (human neutrophil lipocalin) or NGAL (neutrophil gelatinase-associated lipocalin) by flow cytometry or immunohistochemical staining or other corresponding techniques. Such markers may be used as targets of the affinity reagent of the present invention.

Affinity reagents refer generally to any molecule with antibody-like binding properties, in particular to antibodies or fragments or combinations thereof. As used herein, an "antibody" generally refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. The basic immunoglobulin (antibody) structural unit is known to comprise a tetramer or dimer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids, primarily responsible for antigen recognition. The terms "variable light chain" and "variable heavy chain" refer to these variable regions of the light and heavy chains respectively. Optionally, the antibody or the immunological portion of the antibody, can be chemically conjugated to, or expressed as, a fusion protein with other proteins.

Antibodies of the invention include, but are not limited to polyclonal, monoclonal, bispecific, human, humanized or chimeric antibodies, single variable fragments (ssFv), single domain antibodies (such as VHH fragments from camelids or nanobodies), single chain fragments (scFv), Fab fragments, F(ab') fragments, fragments produced by a Fab expression library, anti-idiotypic antibodies and epitope-binding fragments or combinations thereof of any of the above, provided that they retain the original binding properties. Also mini-antibodies and multivalent antibodies such as diabodies, triabodies, tetravalent antibodies and peptabodies can be used in a method of the invention. The immunoglobulin molecules of the invention can be of any class (i.e. IgG, IgE, IgM, IgD and IgA) or subclass of immunoglobulin molecules. Thus, the term antibody, as used herein, also includes antibodies and antibody fragments either produced by the modification of whole antibodies or synthesized de novo using recombinant DNA methodologies.

In a preferred embodiment, the antibody is a camel antibody or a part thereof, for example a camelid VHH-antibody domain.

Heteroconjugate antibodies, comprising two covalently joined antibodies, are also within the scope of the invention. Heteroconjugate antibodies may be made using any convenient cross-linking methods. Suitable cross-linking agents and techniques are well known in the art, and are described in U.S. Pat. No. 4,676,980. Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

Humanized antibody comprising one or more CDRs of antibodies of the invention or one or more CDRs derived from said antibodies can be made using any methods known in the art. For example, four general steps may be used to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; 6,180,370; 5,225,539; 6,548,640.

The term humanized antibody means that at least a portion of the framework regions of an immunoglobulin is derived from human immunoglobulin sequences. The humanized versions of the mouse monoclonal antibodies can, for example, be made by means of recombinant DNA technology, departing from the mouse and/or human genomic DNA sequences coding for H and L chains or from cDNA clones coding for H and L chains. Humanized forms of mouse antibodies can be generated by linking the CDR regions of non-human antibodies to human constant regions by recombinant DNA techniques (Queen et al., 1989; WO 90/07861). Alternatively the monoclonal antibodies used in the method of the invention may be human monoclonal antibodies. Human antibodies can be obtained, for example, using phage-display methods (WO 91/17271; WO 92/01047).

As used herein, humanized antibodies refer also to forms of non-human (e.g. murine, rabbit, rat, camel, llama) antibodies that are specific chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity.

As used herein, human or humanised antibody means an antibody having an amino acid sequence corresponding to that of an antibody produced by a human and/or has been made using any of the techniques for making human antibodies known in the art or disclosed herein. Human antibodies can be selected by competitive binding experiments, or otherwise, to have the same epitope specificity as a particular mouse antibody. Such antibodies are particularly likely to share the useful functional properties of the mouse antibodies. Human polyclonal antibodies can also be provided in the form of serum from humans immunized with an immunogenic agent. Optionally, such polyclonal antibodies can be concentrated by affinity purification using amyloid fibrillar and/or non-fibrillar polypeptides or fragments thereof as an affinity reagent. Monoclonal antibodies can be obtained from serum according to the technique described in WO 99/60846.

A variable region of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. Molec. Biol. 273:927-948)). As used herein, a CDR may refer to CDRs defined by either approach or by a combination of both approaches.

In some embodiments, the invention provides an antibody, which comprises at least one CDR, at least two, at least three, or more CDRs that are substantially identical to at least one CDR, at least two, at least three, or more CDRs of the antibody or peptide of the invention. Other embodiments include antibodies which have at least two, three, four, five, or six CDR(s) that are substantially identical to at least two, three, four, five or six CDRs of the antibodies of the invention or derived from the antibodies of the invention. In some embodiments, the at least one, two, three, four, five, or six CDR(s) are at least about 85%, 86%, 87%, 88%, 89%, 90%, 95%, 96%, 97%, 98%, or 99% identical to at least one, two or three CDRs of the antibody of the invention. It is understood that, for purposes of this invention, binding specificity and/or overall activity is generally retained, although the extent of activity may vary compared to said antibody (may be greater or lesser).

The affinity reagent, antibody or fragment thereof according to the invention may be PEGylated, whereby PEGylation refers to covalent attachment of polyethylene glycol (PEG) polymer chains to the inventive antibody. PEGylation may be routinely achieved by incubation of a reactive derivative of PEG with the target molecule. PEGylation to the antibody can potentially mask the agent from the host's immune system, leading to reduced immunogenicity and antigenicity or increase the hydrodynamic size of the agent which may prolong its circulatory time by reducing renal clearance.

The affinity reagent, antibody or fragment thereof according to the invention may comprise a fragment crystallizable region (Fc region). The Fc region is the tail region of an antibody that interacts with cell surface receptors, known as Fc receptors, and potentially other proteins of the complement system. Fc regions are known in the art and differ according to their Ig isotypes, for example in IgG, IgA and IgD antibody isotypes the Fc region is composed of two identical protein fragments, derived from the second and third constant domains of the antibody's two heavy chains; IgM and IgE Fc regions contain three heavy chain constant domains (CH domains 2-4) in each polypeptide chain. The Fc regions may provide increased stability and/or improved half-life in vivo to the antibodies of the present invention.

Sequence variants of the claimed nucleic acids, proteins and antibodies, for example defined by the claimed % sequence identity, that maintain the said properties of the invention are also included in the scope of the invention. Such variants, which show alternative sequences, but maintain essentially the same binding properties, such as target specificity, as the specific sequences provided are known as functional analogues, or as functionally analogous. Sequence identity relates to the percentage of identical nucleotides or amino acids when carrying out a sequence alignment.

It will be appreciated by those of ordinary skill in the art that, as a result of the degeneracy of the genetic code, there are many nucleotide sequences that encode a polypeptide as described herein. Some of these polynucleotides bear minimal homology or sequence identity to the nucleotide sequence of any native gene. Nonetheless, polynucleotides that vary due to differences in codon usage are specifically contemplated by the present invention. Deletions, substitutions and other changes in sequence that fall under the described sequence identity are also encompassed in the invention.

Protein modifications, which may occur through substitutions, are also included within the scope of the invention. Substitutions as defined herein are modifications made to the amino acid sequence of the protein, whereby one or more amino acids are replaced with the same number of (different) amino acids, producing a protein which contains a different amino acid sequence than the primary protein, preferably without significantly altering the function of the protein. Like additions, substitutions may be natural or artificial. It is well known in the art that amino acid substitutions may be made without significantly altering the protein's function. This is particularly true when the modification relates to a "conservative" amino acid substitution, which is the substitution of one amino acid for another of similar properties. Such "conserved" amino acids can be natural or synthetic amino acids which because of size, charge, polarity and conformation can be substituted without significantly affecting the structure and function of the protein. Frequently, many amino acids may be substituted by conservative amino acids without deleteriously affecting the protein's function.

In general, the non-polar amino acids Gly, Ala, Val, Ile and Leu; the non-polar aromatic amino acids Phe, Trp and Tyr; the neutral polar amino acids Ser, Thr, Cys, Gln, Asn and Met; the negatively charged amino acids Lys, Arg and His; the positively charged amino acids Asp and Glu, represent groups of conservative amino acids. This list is not exhaustive. For example, it is well known that Ala, Gly, Ser and sometimes Cys can substitute for each other even though they belong to different groups.

Conservative amino acid substitutions are not limited to naturally occurring amino acids, but also include synthetic amino acids. Commonly used synthetic amino acids are omega amino acids of various chain lengths and cyclohexyl alanine which are neutral non-polar analogs; citulline and methionine sulfoxide which are neutral non-polar analogs, phenylglycine which is an aromatic neutral analog; cysteic acid which is a positively charged analog and ornithine which is a negatively charged amino acid analog. Like the naturally occurring amino acids, this list is not exhaustive, but merely exemplary of the substitutions that are well known in the art.

A pharmaceutical acceptable carrier in the sense of the present invention may be any non-toxic material that does not interfere in a detrimental sense with the effectiveness of the biological activity of the antibodies of the present invention. Evidently, the characteristics of the carrier will depend on the route of administration. Such a composition may contain, in addition to the active substance and carrier, diluents, fillers, salts, buffers, stabilizers, solubilizers, and other materials well known in the art. Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intra-muscular administration and formulation.

The medicament, otherwise known as a pharmaceutical composition, containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or *acacia*, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyceryl distearate may be employed. They may also be coated. The present invention also refers to a pharmaceutical composition for topical application, oral ingestion, inhalation, or cutaneous, subcutaneous, or intravenous injection. A skilled person is aware of the carriers and additives required for particular application forms.

When a therapeutically effective amount of the active substance of the invention is administered by intravenous, cutaneous or subcutaneous injection, the active substance may be in the form of a pyrogen-free, parenterally acceptable aqueous solution.

As used herein, the term "therapeutically effective amount" means the total amount of each active component of the pharmaceutical composition or method that is sufficient to show a meaningful patient benefit. The amount of active substance in the pharmaceutical composition of the present invention will depend upon the nature and severity of the condition being treated, and on the nature of prior treatments which the patient has undergone. Larger doses may be administered until the optimal therapeutic effect is obtained for the patient, and at that point the dosage is not increased further.

The preparation of such parenterally acceptable solutions, having due regard to pH, isotonicity, stability, and the like, is within the skill in the art. A preferred pharmaceutical composition for intravenous, cutaneous, or subcutaneous injection should contain, in addition to the active subtance, an isotonic vehicle such as Sodium Chloride Injection, Ringers Injection, Dextrose Injection, Dextrose and Sodium Chloride Injection, Lactated Ringers Injection, or other vehicle as known in the art. The pharmaceutical composition of the present invention may also contain stabilizers, preservatives, buffers, antioxidants, or other additives known to those of skill in the art.

The dose of the antibody administered evidently depends on numerous factors well-known in the art such as, e.g., the chemical nature and pharmaceutical formulation of the antibody, and of body weight, body surface, age and sex of the patient, as well as the time and route of administration. For an adult, the dose may exemplarily be between 0.5 µg and 1 g per day, preferably between 0.5 µg and 100 mg per day, more preferably between 1 µg and 100 mg per day, even more preferably between 5 µg and 10 mg per day, even more preferably between 1 µg and 10 mg per day. In a continuous infusion, the dose may exemplarily be between 0.5 µg and 100 mg, preferably between 1 µg and 10 mg per kilogram per minute.

In one embodiment of the invention the isolated bispecific antibody or antibody fragment is intended for use in the treatment of a medical disorder associated with inflammation, preferably rheumatic disorder or auto immune disease with an inflammatory component. Diseases associated with TNF and associated inflammation are known to a skilled person and can be identified by routine assays, such as ELISA or other immunological techniques capable of detecting and providing quantitative or semi-quantitative measurements of TNF from patient samples. Further molecular, cytological, physiological or other assays are known to a skilled person and may be employed to assess inflammation and a potential role of TNF in any given disease.

The rheumatic disorder or auto immune disease with an inflammatory component is preferably selected from Takayasu Arteritis, Giant-cell arteritis, familial Mediterranean fever, Kawasaki disease, Polyarteritis nodosa, cutanous Polyarteritis nodosa, Hepatitis-associated arteritis, Behcet's syndrome, Wegener's granulomatosis, Churg-Strauss syndrome, microscopic polyangiitis, Vasculitis of connective tissue diseases, Hennoch-Schönlein purpura, Cryoglobulinemic vasculitis, Cutaneous leukocytoclastic angiitis, Tropical aortitis, Sarcoidosis, Cogan's syndrome, Wiskott-Aldrich Syndrome, Lepromatous arteritis, Primary angiitis of the CNS, Thromboangiitis obliterans, Paraneoplastic ateritis, Urticaria, Dego's disease, Myelodysplastic syndrome, Eythema elevatum diutinum, Hyperimmunoglobulin D, Allergic Rhinitis, Asthma bronchiale, chronic obstructive pulmonary disease, periodontitis, Rheumatoid Arthritis, atherosclerosis, Amyloidosis, Morbus Chron, Colitis ulcerosa, Autoimmune Myositis, Diabetes mellitus, Multiple sclerosis, Guillain-Barre Syndrome, histiocytosis, Osteoarthritis, atopic dermatitis, periodontitis, chronic rhinosinusitis, Psoriasis, psoriatic arthritis, Microscopic colitis, Pulmonary fibrosis, glomerulonephritis, Whipple's disease, Still's disease, erythema nodosum, otitis, cryoglobulinemia, Sjogren's syndrome, Lupus erythematosus, aplastic anemia, Osteomyelofibrosis, chronic inflammatory demyelinating polyneuropathy, Kimura's disease, systemic sclerosis, chronic periaortitis, chronic prostatitis, idiopathic pulmonary fibrosis, chronic granulomatous disease, Idiopathic achalasia, bleomycin-induced lung inflammation, cytarabine-induced lung inflammation, Autoimmunthrombocytopenia, Autoimmunneutropenia, Autoimmunhemolytic anemia, Autoimmunlymphocytopenia, Chagas' disease, chronic autoimmune thyroiditis, autoimmune hepatitis, Hashimoto's Thyroiditis, atropic thyroiditis, Graves disease, Autoimmune polyglandular syndrome, Autoimmune Addison Syndrome, Pemphigus vulgaris, Pemphigus foliaceus, Dermatitis herpetiformis, Autoimmune alopecia, Vitiligo, Antiphospholipid syndrome, Myasthenia gravis, Stiff-man syndrome, Goodpasture's syndrome, Sympathetic ophthalmia, Folliculitis, Sharp syndrome and/or Evans syndrome, in particular hay fever, periodontitis, atherosclerosis, rheumatoid arthritis, and cancer, preferably rheumatoid arthritis or multiple sclerosis.

Sequences of the invention:

SEQ ID No. 1, TNFα binding domain, single domain antibody, VHH domain:
MGSQVQLQESGGGLVQPGGSLRLSCAASGRTFSDHSGYTYTIGWFRQAPG

KEREFVARIYWSSGNTYYADSVKGRFAISRDIAKNTVDLTMNNLEPEDTA

VYYCAARDGIPTSRSVESYNYWGQGTQVTVSSAGA

SEQ ID No. 2, CDR H1:
GYTFTNHMN

SEQ ID No. 3, CDR H2:
RINPGTGGTSYNVNFKG

SEQ ID No. 4, CDR H3:
GDSYWYFDF

SEQ ID No. 5, CDR L1:
KASKSISKYLA

SEQ ID No. 6, CDR L2:
EGSTLQS

SEQ ID No. 7, CDR L3:
QQHNEYPLT

SEQ ID No. 8, VH domain:
MQVQLQQSGAELVKPGTSVKLSCKASGYTFTNHMNWVKQTTGQGLEWIGR

INPGTGGTSYNVNFKGKATLTVDESSSTAFMQLSSLTPEDSAVYYCARGD

SYWYFDFWGPGTMVTVSGS

SEQ ID No. 9, VL domain:
DVQMTQSPYNLVASPGESVSINCKASKSISKYLAWYQQKPGKANKLLIYE

GSTLQSGIPSRFSGSGSGTDFTLTIRSLEPEDFGLYYCQQHNEYPLTFGS

GTKLEIKRADAAPTVAAAPRGGPEQKLISEEDLNSAVD

SEQ ID 10, entire sequence of preferred Ab:
MGSQVQLQESGGGLVQPGGSLRLSCAASGRTFSDHSGYTYTIGWFRQAPG

KEREFVARIYWSSGNTYYADSVKGRFAISRDIAKNTVDLTMNNLEPEDTA

VYYCAARDGIPTSRSVESYNYWGQGTQVTVSSAGAGSGGGGSGMQVQLQQ

SGAELVKPGTSVKLSCKASGYTFTNHMNWVKQTTGQGLEWIGRINPGTGG

TSYNVNFKGKATLTVDESSSTAFMQLSSLTPEDSAVYYCARGDSYWYFDF

WGPGTMVTVSGSGGGGSGGGGSGGGGSDVQMTQSPYNLVASPGESVSINC

KASKSISKYLAWYQQKPGKANKLLIYEGSTLQSGIPSRFSGSGSGTDFTL

TIRSLEPEDFGLYYCQQHNEYPLTFGSGTKLEIKRADAAPTVAAAPRGGP

EQKLISEEDLNSAVD

SEQ ID No. 11, ScFv:
ATGGGTTCCCAAGTTCAGCTTCAAGAATCTGGTGGAGGACTTGTTCAACC

TGGTGGATCTCTTAGGCTTTCTTGCGCTGCTTCTGGAAGGACTTTCTCTG

ATCACTCTGGATACACTTACACTATTGGATGGTTCAGACAGGCTCCAGGA

AAAGAGAGAGTTCGTTGCTAGGATCTACTGGTCATCTGGAAACACTTA

CTACGCTGATTCTGTGAAGGGAAGATTCGCTATTTCTAGGGATATTGCTA

AGAACACTGTGGATCTTACTATGAACAACCTTGAGCCAGAGGATACTGCT

GTTTACTATTGCGCTGCTAGGGATGGAATTCCAACTTCTAGATCTGTGGA

GTCTTACAACTACTGGGGACAGGGAACTCAAGTGACTGTTTCTTCTGCCG

GCGCG

SEQ ID No. 12, CDRH1:
GGTTATACCTTTACCCGCAATCATATGAAT

SEQ ID No. 13, CDRH2:
CGTATTAATCCGGGTACAGGTGGCACCAGCTATAATGTGAATTTTAAGG
C

SEQ ID No. 14, CDRH3:
GG1CGATAGCTATTGGTATTTTGATTTT

SEQ ID No. 15, CDRL1:
AAAGCCAGCAAAAGCATTAGCAAATATCTGGCA

SEQ ID No. 16, CDRL2:
GAAGGTAGCACCCTGCAGAGC

SEQ ID No.17, CDRL3:
CAGCAGCATAATGAATATCCGCTGACC

SEQ ID No. 18, VH:
ATGCAGGTTCAGCTGCAGCAGAGCGGTGCAGAACTGGTTAAACCGGGTAC

AAGCGTTAAACTGAGCTGTAAAGCAAGCGGTTATACCTTTACCCGCAATC

ATATGAATTGGGTGAAACAGACCACCGGTCAGGGTCTGGAATGGATTGGT

CGTATTAATCCGGGTACAGGTGGCACCAGCTATAATGTGAATTTTAAGG

CAAAGCAACCCTGACCGTTGATGAAAGCAGCAGCACCGCATTTATGCAGC

TGAGCAGCCTGACACCGGAAGATAGCGCAGTGTACTACTGTGCACGTGG1

CGATAGCTATTGGTATTTTGATTTTGGGGTCCGGGTACAATGGTTACCG

TTAGCGGTAGC

SEQ ID No. 19, VL:
GATGTTCAGATGACCCAGAGCCCGTATAATCTGGTTGCATCTCCGGGTGA

AAGCGTTAGCATTAATTGCAAAGCCAGCAAAAGCATTAGCAAATATCTGG

CATGGTATCAGCAGAAACCGGGTAAAGCAAATAAACTGCTGATTTATGAA

GGTAGCACCCTGCAGAGCGGTATTCCGAGCCGTTTTAGCGGTTCTGGTAG

CGGCACCGATTTTACCCTGACCATTCGTAGCCTGGAACCGGAAGATTTTG

GTCTGTATTATTGCCAGCAGCATAATGAATATCCGCTGACCTTTGGTAGC

GGTACAAAACTGGAAATTAAACGTGCAGATGCAGCACCGACCGTTGCAGC

AGCTCCGCGTGGTGGTCCGGAACAGAAACTGATTAGCGAAGAAGATCTGA

ATAGCGCAGTTGATC

SEQ ID No. 20, entire sequence of preferred Ab:
ATGGGTTCCCAAGTTCAGCTTCAAGAATCTGGTGGAGGACTTGTTCAACC

TGGTGGATCTCTTAGGCTTTCTTGCGCTGCTTCTGGAAGGACTTTCTCTG

ATCACTCTGGATACACTTACACTATTGGATGGTTCAGACAGGCTCCAGGA

AAAGAGAGAGTTCGTTGCTAGGATCTACTGGTCATCTGGAAACACTTA

CTACGCTGATTCTGTGAAGGGAAGATTCGCTATTTCTAGGGATATTGCTA

AGAACACTGTGGATCTTACTATGAACAACCTTGAGCCAGAGGATACTGCT

GTTTACTATTGCGCTGCTAGGGATGGAATTCCAACTTCTAGATCTGTGGA

GTCTTACAACTACTGGGGACAGGGAACTCAAGTGACTGTTTCTTCTGCCG

-continued

```
GCGCGGGATCCGGTGGTGGTGGTAGCGGTATGCAGGTTCAGCTGCAGCAG

AGCGGTGCAGAACTGGTTAAACCGGGTACAAGCGTTAAACTGAGCTGTAA

AGCAAGCGGTTATACCTTTACCCGCAATCATATGAATTGGGTGAAACAGA

CCACCGGTCAGGGTCTGGAATGGATTGGTCGTATTAATCCGGGTACAGGT

GGCACCAGCTATAATGTGAATTTTAAAGGCAAAGCAACCCTGACCGTTGA

TGAAAGCAGCAGCACCGCATTTATGCAGCTGAGCAGCCTGACACCGGAAG

ATAGCGCAGTGTACTACTGTGCACGTGG1CGATAGCTATTGGTATTTTGA

TTTTTGGGGTCCGGGTACAATGGTTACCGTTAGCGGTAGCGGTGGTGGCG

GTTCTGGTGGTGGTGGCTCAGGTGGCGGTGGTTCTGATGTTCAGATGACC

CAGAGCCCGTATAATCTGGTTGCATCTCCGGGTGAAAGCGTTAGCATTAA

TTGCAAAGCCAGCAAAAGCATTAGCAAATATCTGGCATGGTATCAGCAGA

AACCGGGTAAAGCAAATAAACTGCTGATTTATGAAGGTAGCACCCTGCAG

AGCGGTATTCCGAGCCGTTTTAGCGGTTCTGGTAGCGGCACCGATTTTAC

CCTGACCATTCGTAGCCTGGAACCGGAAGATTTTGGTCTGTATTATTGCC

AGCAGCATAATGAATATCCGCTGACCTTTGGTAGCGGTACAAAACTGGAA

ATTAAACGTGCAGATGCAGCACCGACCGTTGCAGCAGCTCCGCGTGGTGG

TCCGGAACAGAAACTGATTAGCGAAGAAGATCTGAATAGCGCAGTTGATC

SEQ ID No. 21, Sequence of A9:
MGSQVQLQESGGGLVQPGGSLRLSCAASGRTFSDHSGYTYTIGWFRQAPG

KEREFVARIYWSSGNTYYADSVKGRFAISRDIAKNTVDLTMNNLEPEDTA

VYYCAARDGIPTSRSVESYNYWGQGTQVTVSSAGAGSGGGGSGMQVQLQQ

SGAELVKPGTSVKLSCKASGYTFTRNHMNWVKQTTGQGLEWIGRINPGTG

GTSYNVNFKGKATLTVDESSSTAFMQLSSLTPEDSAVYYCARGDSYWYFD

FWGPGTMVTVSGSGGGSGGGGSGGGGSDVQMTQSPYNLVASPGESVSIN

CKASKSISKYLAWYQQKPGKANKLLIYEGSTLQSGIPSRFSGSGSGTDFT

LTIRSLEPEDFGLYYCQQHNEYPLTFGSGTKLEIKRADAAPTVAAAPRGG

PEQKLISEEDLNSAVDLEHHHHHH

SEQ ID No. 22, Sequence of mA9:
MGSQVQLQESGGGLVQPGGSLRLSCAASGRTFSDHSGYTYTIGWFRQAPG

KEREFVARIYWSSGNTYYADSVKGRFAISRDIAKNTVDLTMNNLEPEDTA

VYYCAARDGIPTSRSVESYNYWGQGTQVTVSSAGAGSGGGGSGMQVQLQQ

SGAELVKPGTSVKLSCKASGGGGSGGGGSWVKQTTGQGLEWIGGGGGSG

GGGSGGGGSKATLTVDESSSTAFMQLSSLTPEDSAVYYCARGGGSGGGG

SWGPGTMVTVSGSGGGSGGGGSGGGGSDVQMTQSPYNLVASPGESVSIN

CGGGGSGGGGSGWYQQKPGKANKLLIYGSGGGSGGIPSRFSGSGSGTDFT

LTIRSLEPEDFGLYYCGGGSGGGGSFGSGTKLEIKRADAAPTVAAAPRGG

PEQKLISEEDLNSAVDLEHHHHHH
```

The equipment and means for carrying out the invention are commonly known to one skilled in the art. Material for cell separation includes but is not limited to MACS columns, microbeads and Percoll for density gradients to isolate immune cells from bone marrow, spleen, and liver.

Material for biochemistry and molecular biology include reagents for purification and analysis of proteins, gene arrays, and oligonucleotide primers. Antibodies for cell surface receptors, cytokines and their blockers are used to assess the effects of genetic or pharmacologic TNF deficiency an immune cells by flow cytometry. Appropriate laboratory equipment is commonly known to a skilled person and may encompass in particular, such devices as AUTOMACS, FACS Calibur, FACS-LSR II, FACS-Sorter Aria, FACS-DIVA, fluorescence microscopes, confocal miscroscopes, surface plasmon resonance system ProteOn, Affymetrix hybridization station and Light cycler PCR machines.

FIGURES

The figures provided herein represent examples of particular embodiments of the invention and are not intended to limit the scope of the invention. The figures are to be considered as providing a further description of possible and potentially preferred embodiments that enhance the technical support of one or more non-limiting embodiments.

FIG. 1: TNF is critical cytokine for collagen-induced arthritis (CIA) development
A. Wild type (WT) and TNF deficient (TNF KO) mice were immunized with chicken collagen type II (100 mcg) emulsified in complete Freund's adjuvant (M.Tb concentration—5 mg/ml) twice with 3-week interval. Arthritis incidence was monitored daily. B. Cells were isolated from spleen and draining lymph nodes at day 14 after 2nd immunization and were restimulated with anti-CD3 (1 mcg/ml) and anti-CD28 (0.1 mcg/ml) in the presence of brefeldin A (5 mcg/ml) and cytokine production (IFNg, IL-17) by CD4+ T cells were measured by FACS.

Figure 2:
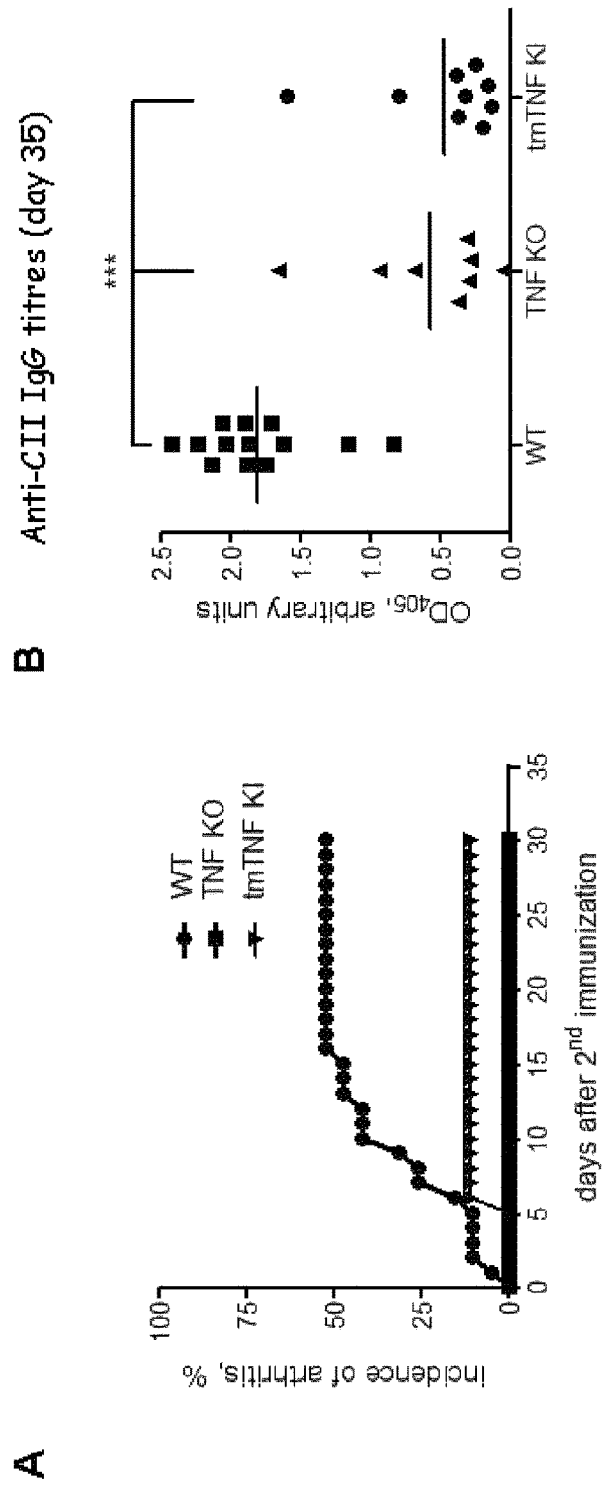

FIG. 2: Soluble TNF is critical for CIA induction
A. Wild type (WT), TNF deficient (TNF KO) and mice expressing only transmembrane form of TNF (tmTNF KI) were immunized with chicken collagen type II (100 mcg) emulsified in complete Freund's adjuvant (M.Tb concentration—5 mg/ml) twice with 3-week interval. Arthritis incidence was monitored daily. B. Sera from various mouse strains was collected at day 14 after second immunization and anti-collagen IgG titres were measured by ELISA.

Figure 3:
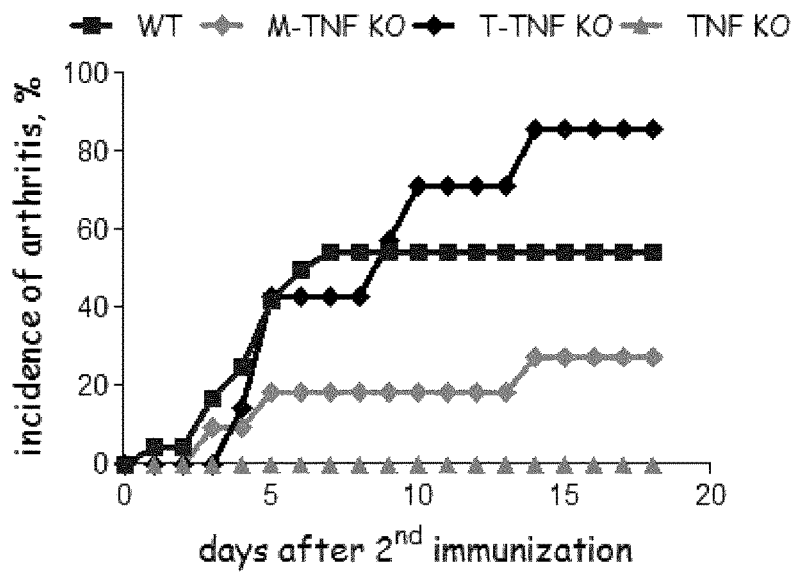

FIG. 3: Non-redundant functions of TNF produced by T cells and myeloid cells in collagen-induced arthritis induction
Wild type (WT), TNF deficient (TNF KO) mice lacking TNF in T cells (T-TNF KO), in myeloid cells (M-TNF KO) were immunized with chicken collagen type II (100 mcg) emulsified in complete Freund's adjuvant (M.Tb concentration—5 mg/ml) twice with 3-week interval. Arthritis incidence was monitored daily.

Figure 4:
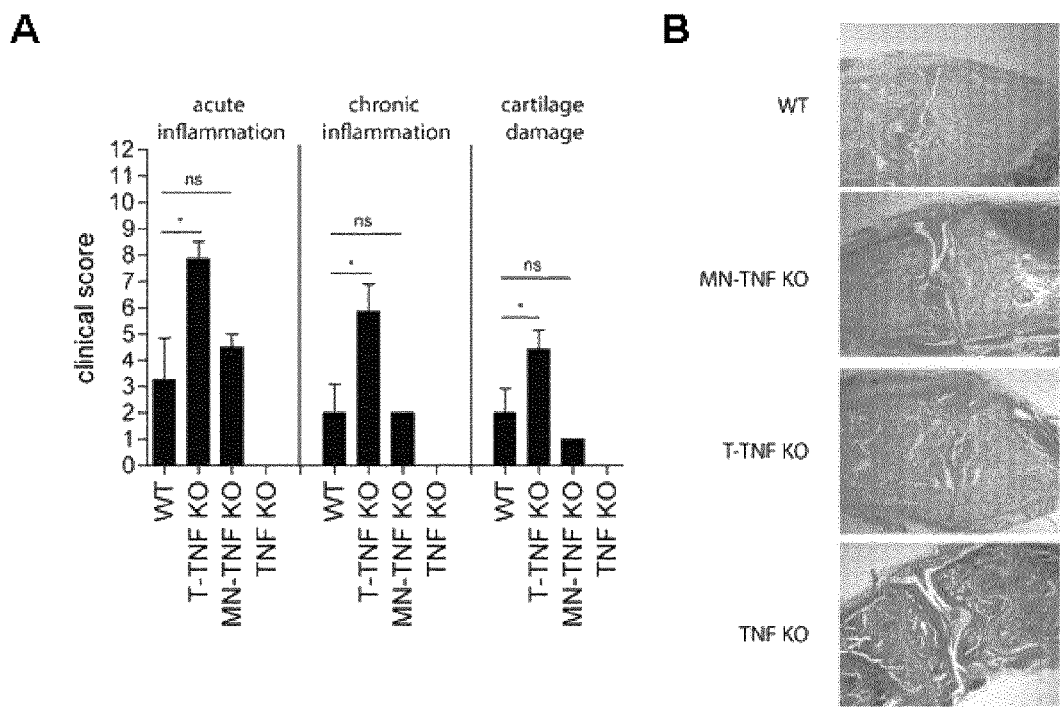

FIG. 4: Non-redundant functions of TNF produced by T cells and myeloid cells in CIA induction
A. Histological assessment of arthritis in mice with TNF ablation in various cell types. B. Representative tissue sections of knee joints stained with heamotoxylin and eosin.

Figure 5:
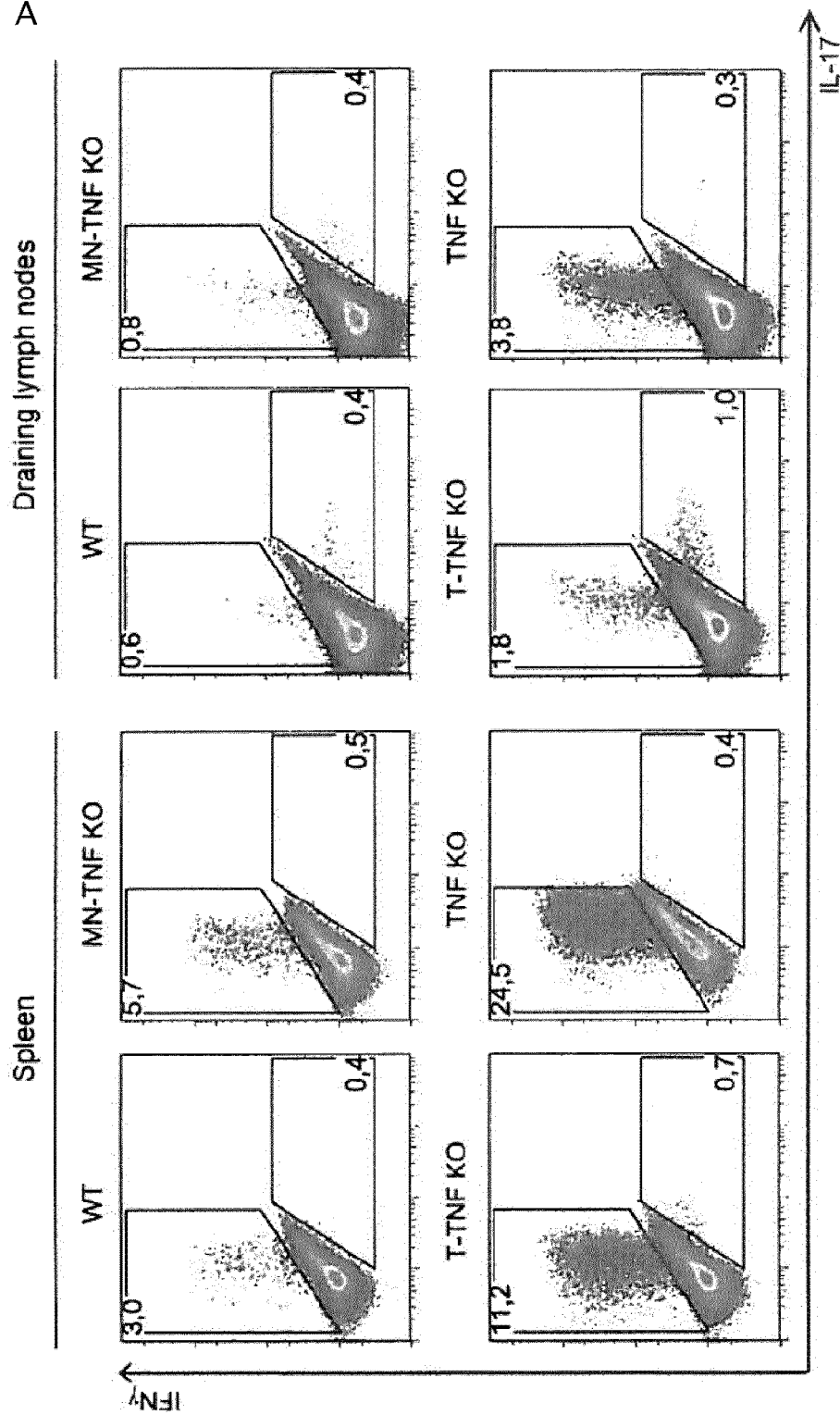
Figure 5:
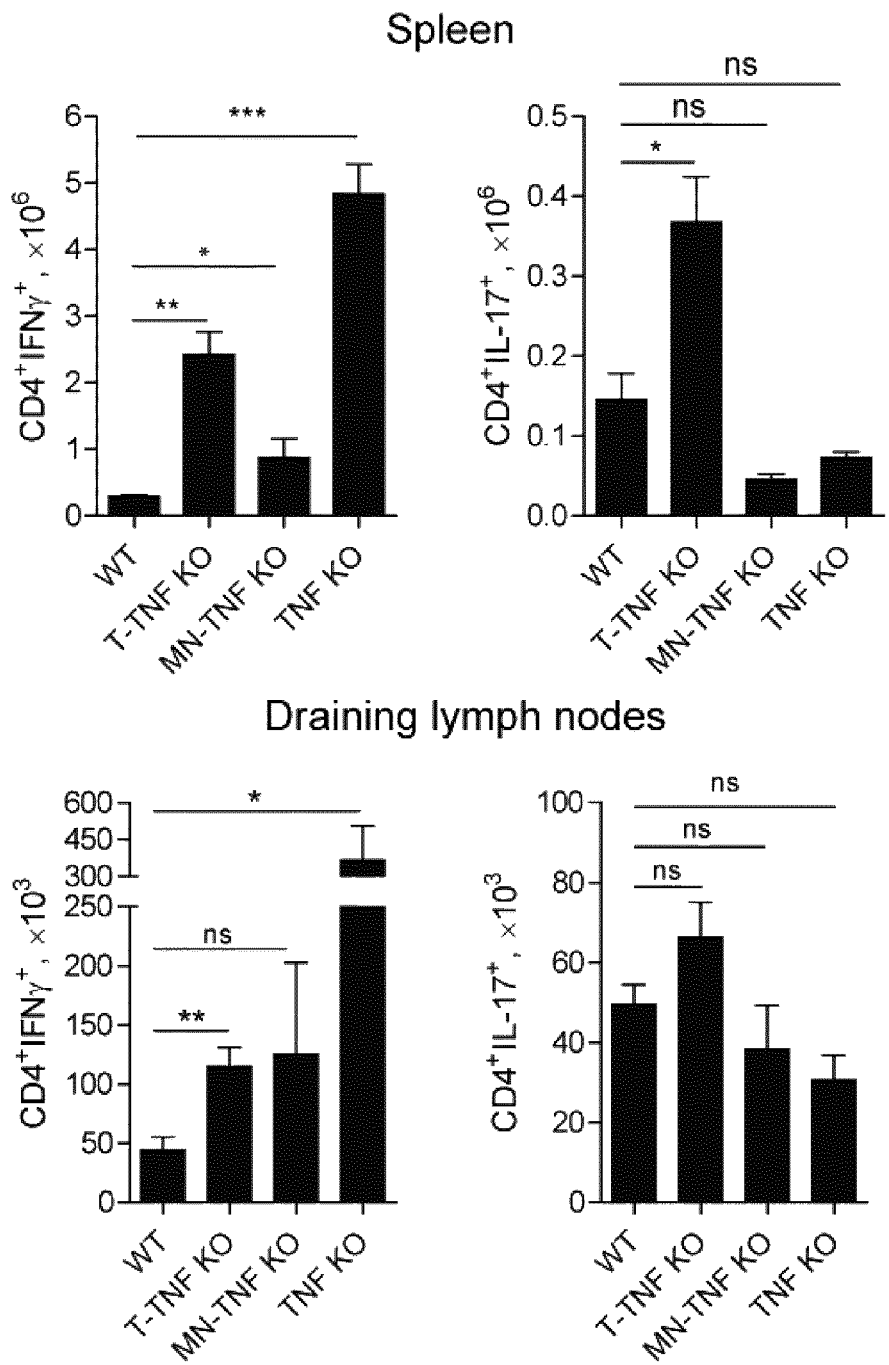

FIG. 5: T-cells are the main cellular source of TNF controlling autoreactive Th development during CIA
A. Representative FACS dot plots of cytokine-producing T cells at day 14 after arthritis induction in spleen and draining lymph nodes. B. Number of IL-17 and IFNg— producing CD4 T cells at day 14 after immunization in spleen and draining lymph nodes.

FIG. 6: B-cell derived TNF exacerbates CIA severity
A. Wild type (WT), and mice lacking TNF in B cells (B-TNF KO) were immunized with chicken collagen type II (100 mcg) emulsified in complete Freund's adjuvant (M.Tb concentration—5 mg/ml) twice with 3-week interval. Arthritis incidence was monitored daily. B. Arthritis severity in mice lacking TNF production by B cells.

Figure 7:
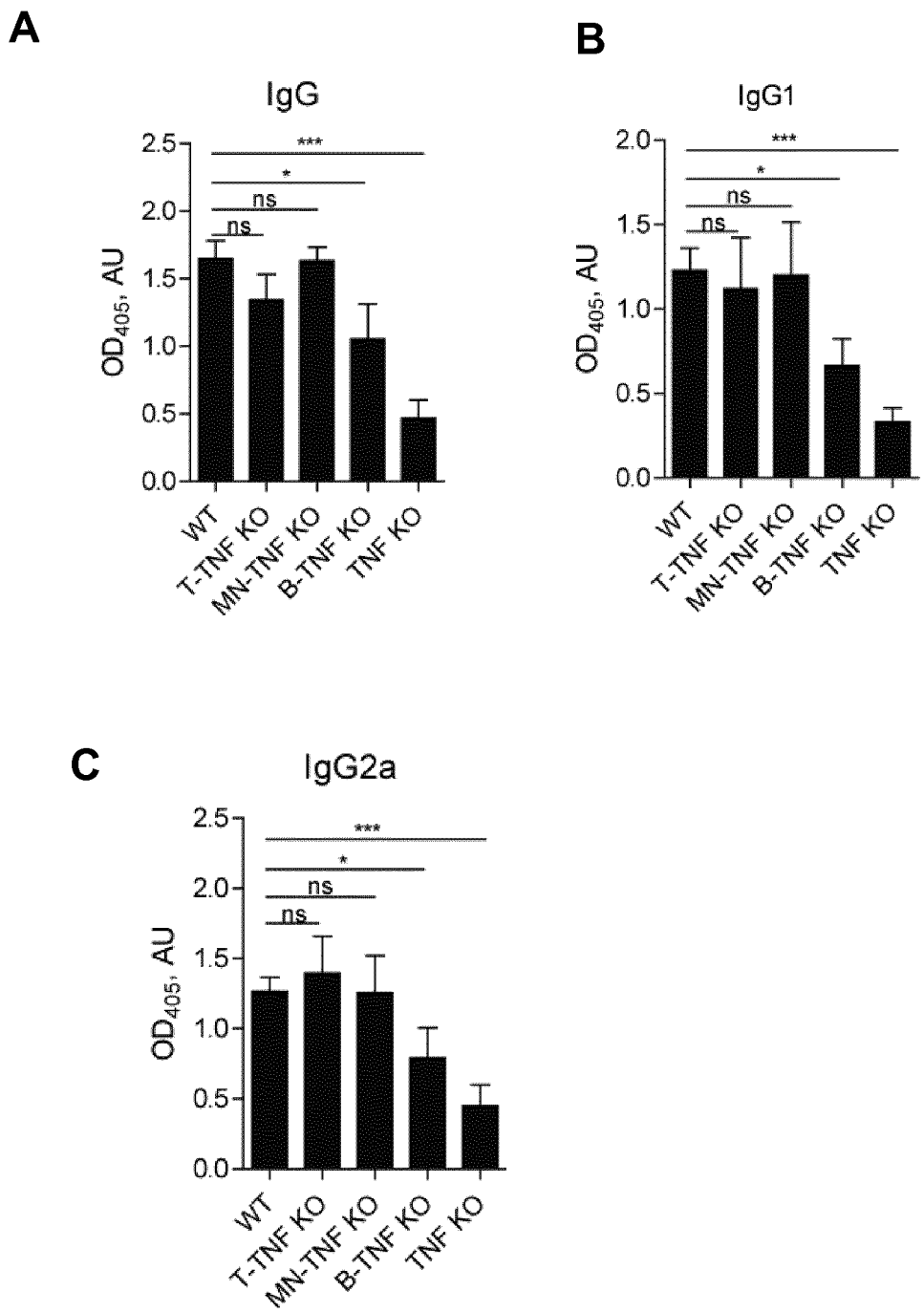

FIG. 7: B-cell derived TNF regulates anti-collagen antibody production

Sera from various mouse strains was collected at day 14 after second immunization and anti-collagen IgG (A), IgG1 (B), IgG2a (C) titres were measured by ELISA.

FIG. 8: Concomitant ablation of TNF produced by T and B cells results in more severe arthritis manifestation A. Wild type (WT), and mice lacking TNF in B cells (B-TNF KO) were immunized with chicken collagen type II (100 mcg) emulsified in complete Freund's adjuvant (M.Tb concentration—5 mg/ml) twice with 3-week interval. Arthritis incidence was monitored daily. B. Arthritis severity in mice lacking TNF production by B cells and T cells at day 14 after second immunization.

Figure 9:
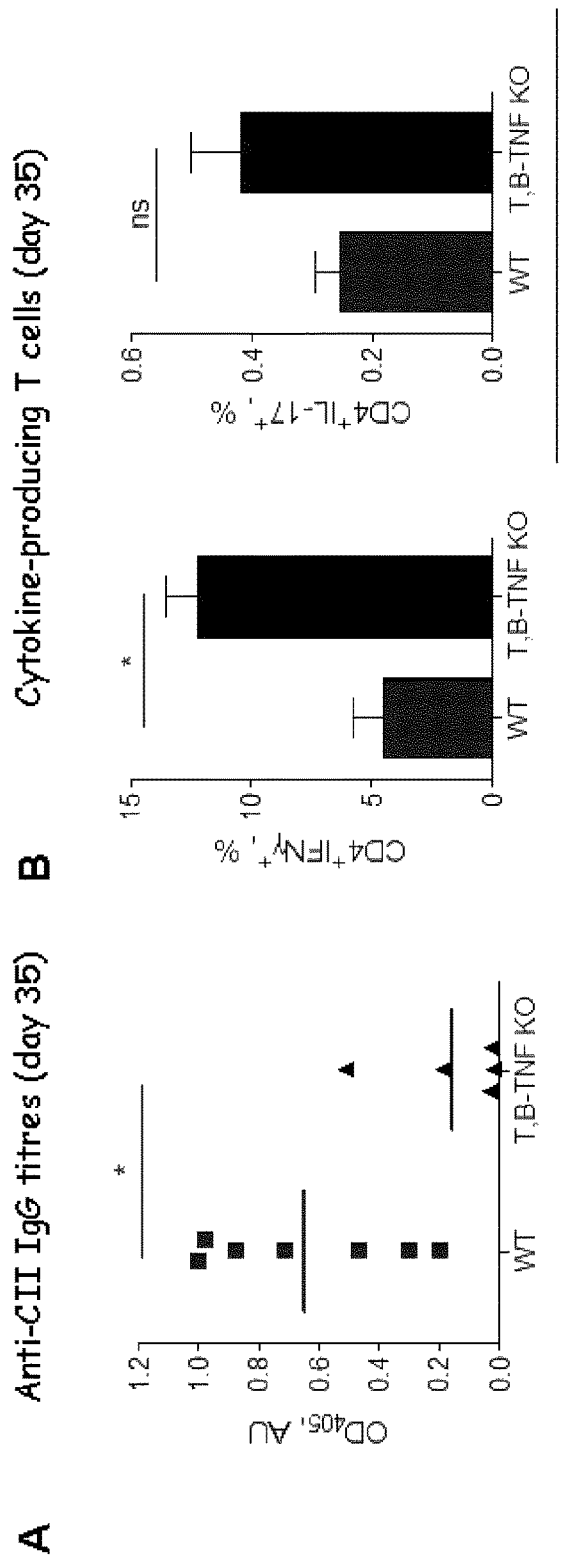

FIG. 9: Severe CIA in T,B-TNF KO is associated with increased autoreactive T cell development A. Sera from WT and mice lacking TNF expression in T and B cells was collected at day 14 after second immunization and anti-collagen IgG titres were measured by ELISA. B. Cells were isolated from spleen and draining lymph nodes at day 14 after 2nd immunization and were restimulated with anti-CD3 (1 mcg/ml) and anti-CD28 (0.1 mcg/ml) in the presence of brefeldin A (5 mcg/ml) and cytokine production (IFNg, IL-17) by CD4+ T cells were measured by FACS.

Figure 10:
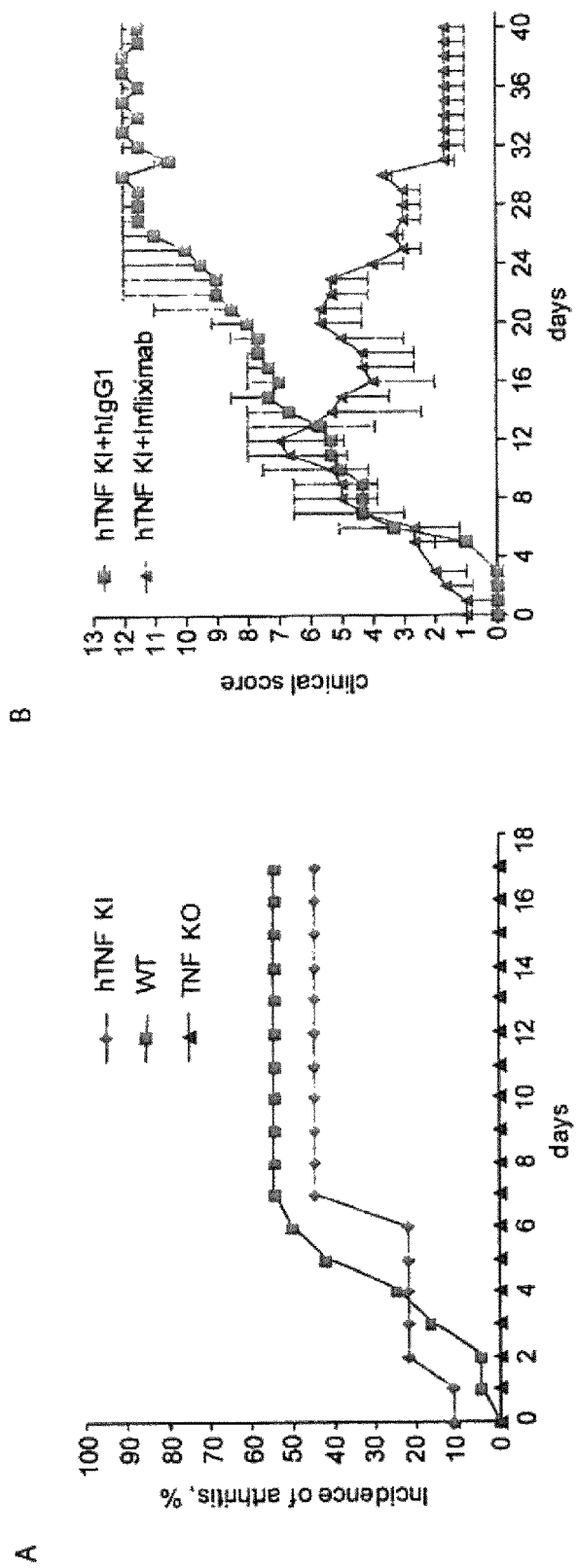

FIG. 10: Humanized knock-in TNF mice develop collagen-induced arthritis which is mediated by hTNF and can be successfully treated with Infliximab.

A. Incidence of arthritis in hTNF KI, C57Bl/6 (WT) and TNF KO mice. B. Infliximab therapy reverses development of established arthritis in hTNF knock-in mice. Clinical score of arthritic hTNF knock-in mice treated either with human IgG1 (10 mg/kg) or Infliximab (10 mg/kg) once per week (starting from day 12 after 2nd immunization).

Figure 11:
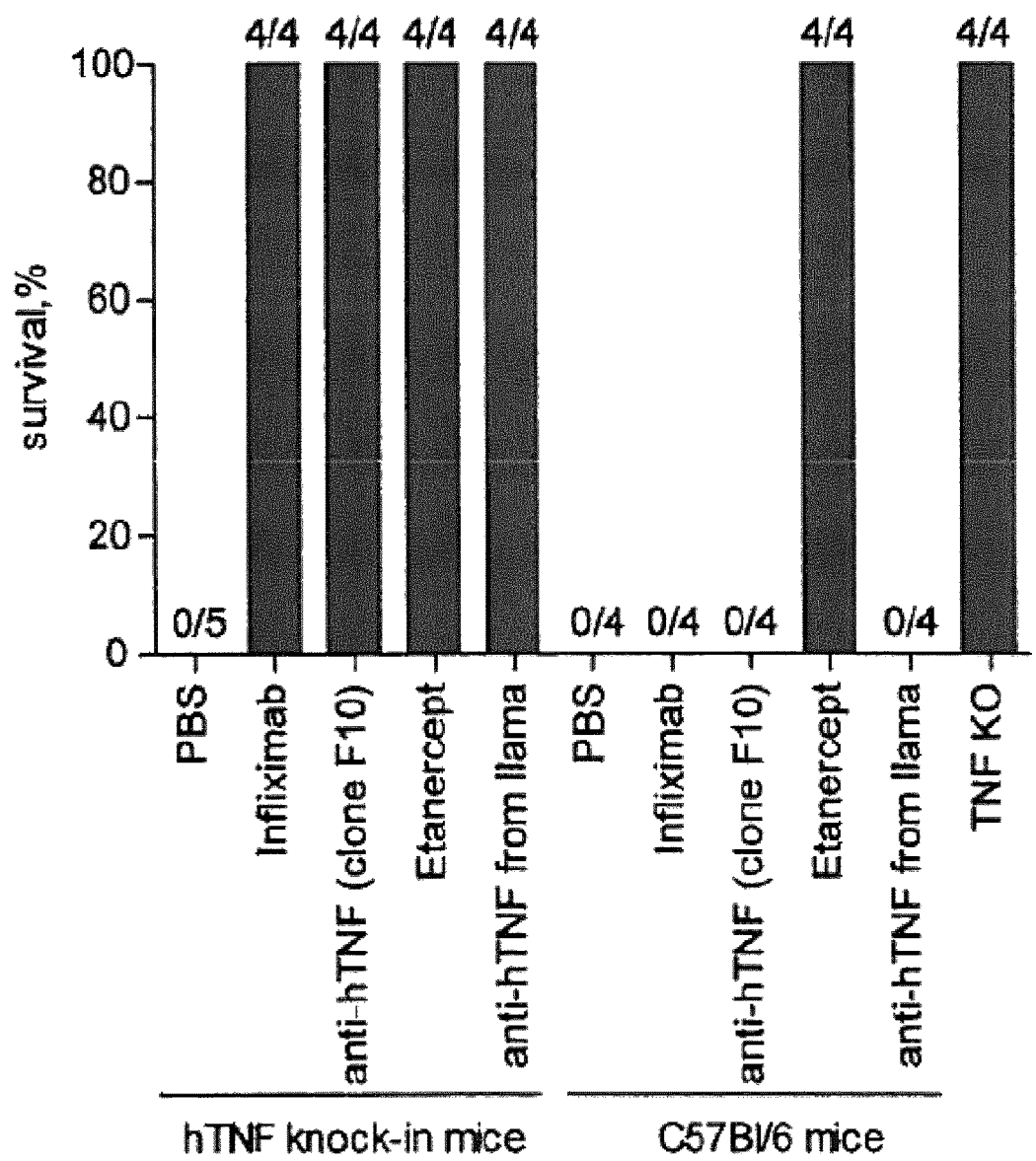

FIG. 11: LPS/D-Gal systemic toxicity in hTNF knock-in mice can be blocked by specific anti-hTNF agents Mice were injected intraperitoneally with LPS (10 mcg/mouse) and D-Galactosamine (20 mg/mouse). 30 min later various TNF blockers were administered intraperitoneally at following concentrations: Infliximab 1 mg/mouse; anti-hTNF (clone F10)-1 mg/mouse; Etanercept—1 mg/mouse; anti-hTNF derived from Llama and produced in bacteria, 300 mcg/mouse. Survival was observed during 24 hours.

Figure 12:
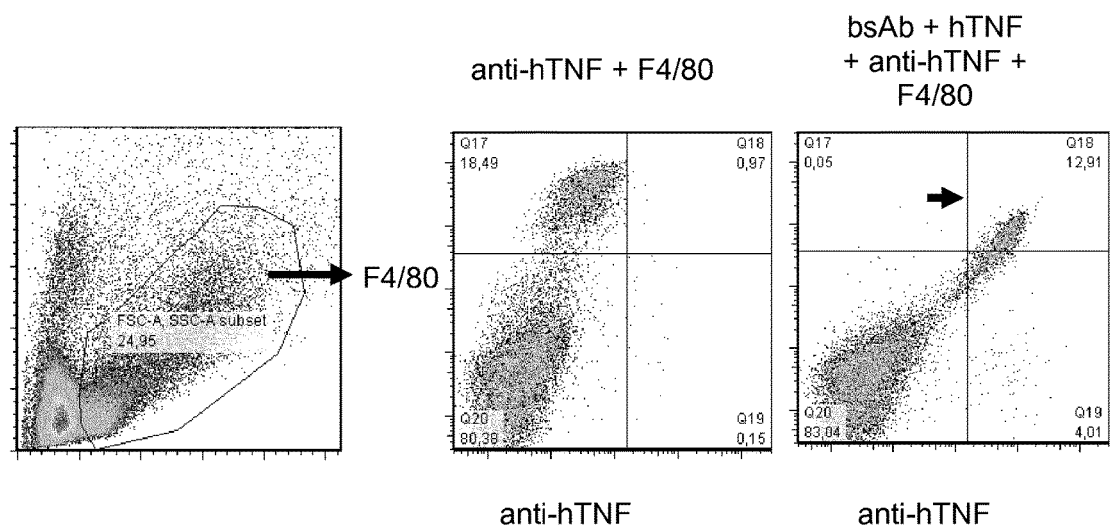

FIG. 12: Bispecific antibody A9 with anti-TNF and anti-F4/80 moieties binds to hTNF Peritoneal cavity cells were isolated from WT animals and incubated with bispecific antibody A9 (2 mcg/ml), followed by incubation with hTNF (10 mcg/ml), anti-hTNF (clone: A2; Miltenyi Biotec) and anti-F4/80 (clone: A3-1) antibodies. Cells were acquired using FACSAria (BDBiosciences) and were analyzed using Flow Jo (Treestar Inc.,)

Figure 13:
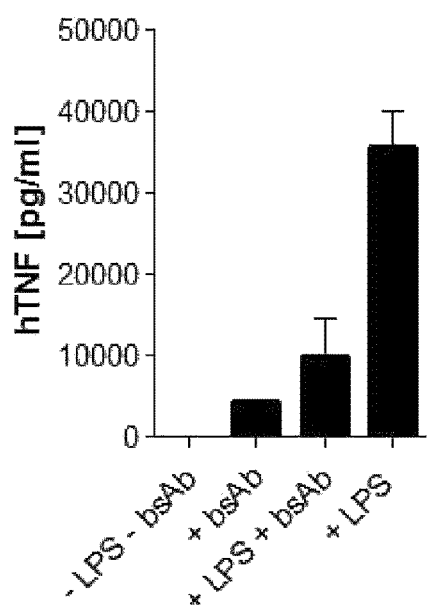

FIG. 13: Bispecific antibody A9 blocks production of human TNF in vitro

Bone-marrow derived macrophages (106 cells) were pre-incubated with bispecific antibody A9 and were activated with LPS (100 ng/ml), hTNF production in supernatant was measured after 4 hours after LPS addition.

FIG. 14: Bispecific antibody A9 with anti-TNF and anti-F4/80 binding moieties

A schematic representation of a preferred bispecific antibody with anti-TNF and anti-F4/80 binding moieties is provided, in addition to a preferred sequence (SEQ ID No. 21) of such an antibody.

FIG. 15: Sequence of bispecific antibody A9 (SEQ ID No. 21) (A) and control antibody mA9 (SEQ ID No. 22) (B). Domains, linkers, CDRs and His-tag are highlighted.

Figure 16:
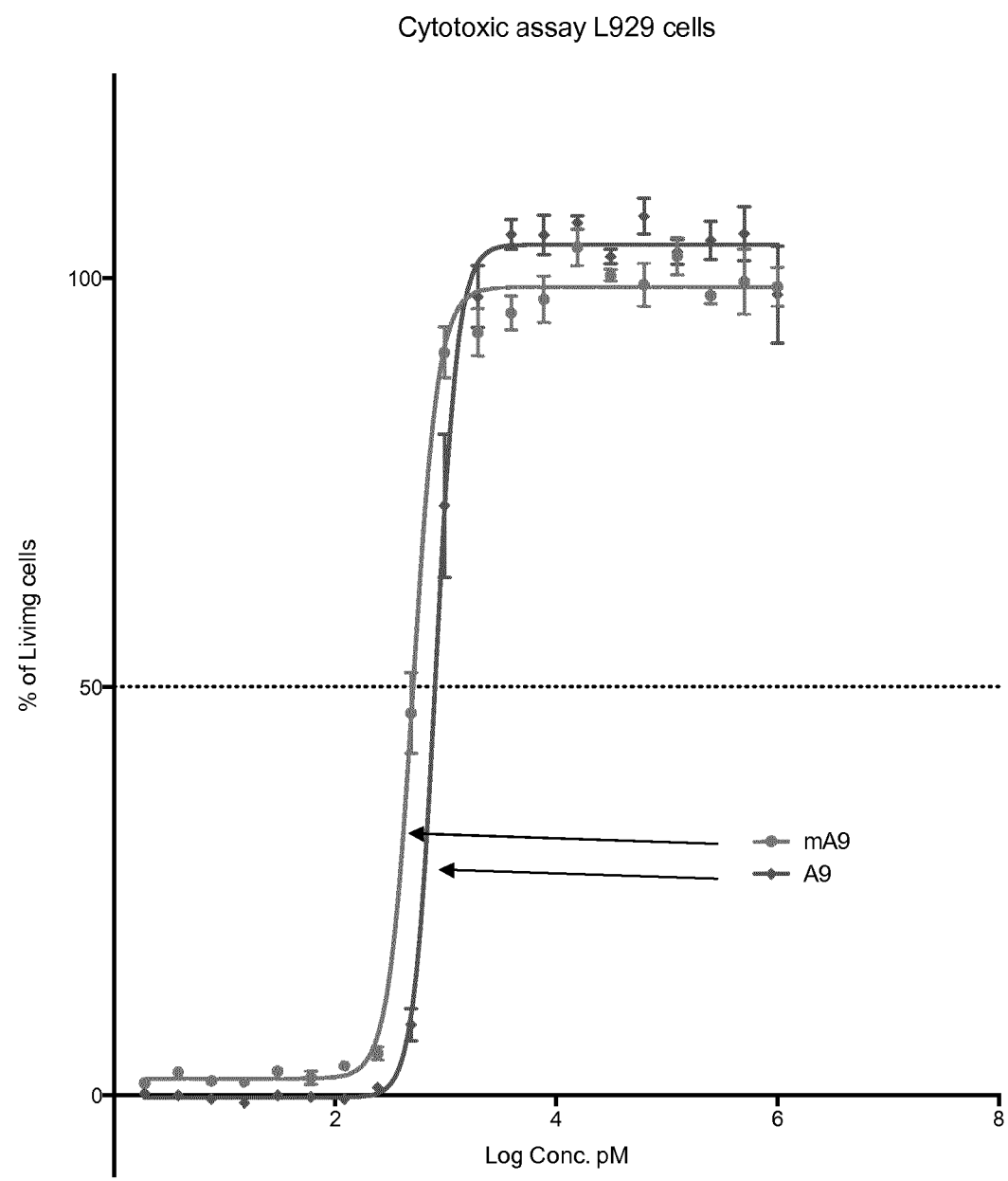

FIG. 16: Cytotoxic assay on L929 cells to characterize neutralizing properties of A9 and mA9. Percentage of surviving cell at different concentrations of A9 and mA9 are plotted.

Figure 17:
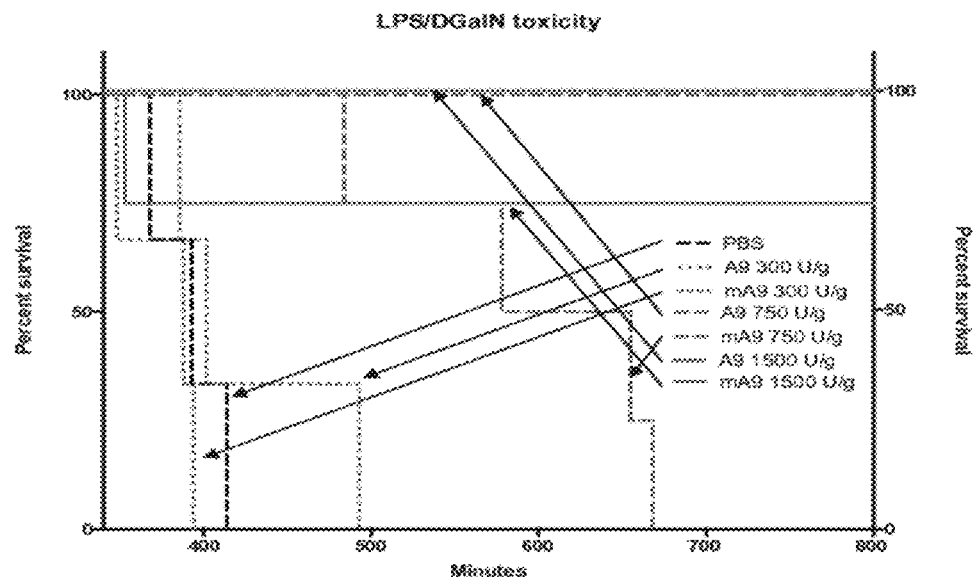

FIG. 17: Ablation of LPS/D-Galactosamine induced acute hepatotoxicity by various anti-hTNF Abs (in humanized mice). Minutes after LPS/D-GalN injection (inhibitors were injected 30 min before).

Figure 18:
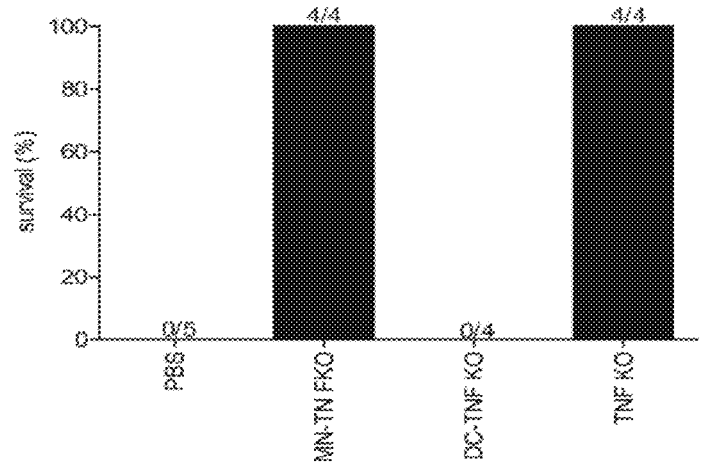

FIG. 18: Ablation of TNF produced by dendritic cells is dispensable for LPS/D-Gal toxicity.

EXAMPLES

The examples provided herein represent practical support for particular embodiments of the invention and are not intended to limit the scope of the invention. The examples are to be considered as providing a further description of possible and potentially preferred embodiments that demonstrate the relevant technical working of one or more non-limiting embodiments.

The invention utilises a CIA model to show that pathogenic and protective TNF are produced by distinct subsets of cells using a unique panel of mice lacking TNF production by specific cell types (for example T cells, B cells or macrophages).

The invention further relates to novel reagents for neutralising human TNF, and because the disease models are in mice, mice "humanized" for the TNF system have been used. The most advanced and convenient is the 'knock-in' mouse in which case the human TNF gene with all its regulatory elements has been placed into exact position of its murine counterpart. These mice are healthy, and they can be induced to develop diseases, such as CIA, which are mediated by human TNF.

The invention further relates to novel bioengineered anti-TNF reagents for example TNF-binding "modules" cloned out from unusual single-domain antibodies produced in camelids (Coppieters et al. 2006, Plagmann et al. J. Biotechnol. 2009). In particular, the invention relates to bi-specific reagents allowing TNF blockade in specific compartments or cell types or lineages.

Distinct Sources of Pathogenic TNF in Disease: Experimental Arthritis in Mice with Conditional TNF Ablation Having in mind the hypothesis that some cellular sources of TNF may be pathogenic while others are neutral or even protective; the inventors induced experimental arthritis in mice with selective TNF depletion in macrophages/neutrophils or in T cells (Grivennikov et al. 2005). Protocol of CIA was adjusted for C57Bl/6 mice and resulted in 50% of wild-type mice developing the disease while TNF KO mice were completely protected (FIG. 1A). Notably, complete ablation of TNF resulted in dramatic increase of autoreactive cytokine producing T cells (FIG. 1B). Moreover, mice expressing only transmembrane form of TNF are largely protected from arthritis development (FIG. 2A) and do not develop autoantibodies directed to type II collagen (FIG. 2B), indicating that it is soluble TNF that plays a pathogenic role in arthritis induction.

Unexpectedly, mice with cell type-restricted TNF ablation showed contrasting phenotypes. Mice with macrophage/neutrophil-restricted TNF gene deletion demonstrated both a lower disease frequency and a lower clinical score in the animals which did develop arthritis (FIG. 3, 4A, 4B). On the contrary, more than 80% of mice with TNF ablation in T cells developed arthritis and the average clinical parameters appeared significantly more severe than in control mice (FIG. 3, 4A, 4B). This striking observation indicates that TNF produced by T cells plays a direct or indirect protective role in arthritis.

Analysis of T Cell Compartments in Mice with Complete or Partial TNF Ablation in the Course of Experimental Arthritis The inventors, as well as others (see Notley et al. 2008) have observed increased numbers of autoreactive effector T cells in lymphoid organs of TNF- or TNFRI-deficient mice during collagen-induced arthritis. This prompted the analysis of specific T cell compartments in mice with partial TNF deficiencies, and uncovered increased numbers of IFNgamma-producing T cells in MN-TNF KO, T-TNF KO and TNF KO mice (FIG. 5A, 5B), indicating that even partial TNF ablation may lead to increased development of autoreactive T cells in spleen. Analysis of cytokine-producing T cells in draining lymph nodes revealed and highlighted the critical role of T-cell derived TNF, but not of TNF expressed by macrophages and neutrophils, in generation of IFNγ and IL-17 producing T cells. Taken together, the data indicated that TNF produced by T cells have protective functions in arthritis by limiting autoreactive T cell development.

Pathogenic Role of B Cell-Derived TNF in Arthritis Severity

Taking into account that TNF produced by B cells is important for antibody production via maintenance of germinal centers (Endres et al JEM 1999; Tumanov et al., 2010), the inventors further addressed the role of TNF produced by B cells in arthritis development. Mice lacking TNF production by B cells developed arthritis with normal incidence (FIG. 6A), however, with significantly reduced severity (FIG. 6B). This correlated with significantly reduced autoantibody production (FIG. 7), suggesting that B-cell derived TNF regulates arthritis severity via autoantibody production. Finally, concomitant ablation of TNF production by T and B-lymphocytes resulted in arthritis with higher incidence and enhanced severity (FIG. 8), characterized by lack of autoantibody development (FIG. 9A) and increased numbers of autoreactive cytokine-producing T cells (FIG. 9B). Altogether, these results showed that B cell derived TNF regulate arthritis severity.

Characterization of Humanized Knock-in Mouse, Producing Human TNF

One of the problems preventing in-depth studies of clinically used TNF blockers in mouse models of autoimmune diseases is due to the fact that most of the blockers cannot neutralize murine TNF. Recently the inventors developed two types of 'humanized' mice in which case human TNF can functionally substitute its murine counterpart in all homeostatic and protective functions analyzed so far (Liepinsh et al. 2009). More recently a more advanced "humanized" model has been developed—a "knock-in" of the human TNF gene into murine TNF locus. These mice are easier to breed and maintain, and thus they are being used in most of the studies. In particular, microarchitecture of lymph nodes, Peyer's patches and the spleen is normal and comparable to that of WT animals. Since regulation of TNF expression appears normal in these mice, they do not develop spontaneous diseases as some of previously characterized TNF transgenic mice which are widely used in arthritis research (Keffer et al. 1991). Of note, mice which develop spontaneous polyarthritis (Keffer et al. 1991) have some other phenotypic features making them difficult to breed and maintain. Experimental disease states in which TNF is known to play a role, including CIA, can be induced in these novel humanized mice, implicating that it is human, and not mouse TNF, that is making pathogenic contribution (FIG. 10A). Moreover, clinically used TNF blockers, such as Infliximab, can be used to ameliorate the disease (FIG. 10B). These mice are a useful tool for uncovering the differences in action of various TNF blockers, as they now can be compared side-by-side in the same model animal.

The Role of Pathogenic and Protective TNF Using Cell-Type-Specific Gene-Inactivated Mice in M. tuberculosis Infection Models The role of TNF produced by macrophages and neutrophils, or by T-cells was investigated in M. tuberculosis infection models, using cell-specific gene-inactivated mice. Experimental analysis shows that TNF produced by myeloid cells is involved only in control of pulmonary M. tuberculosis replication during acute, but not persistent, infection. Transient susceptibility to M. tuberculosis occurred during TNF depletion from macrophages, but infection still recruited activated, TNF-producing CD4+ and CD8+ T-cells and controlled chronic infection. Thus, TNF produced by myeloid cells regulates pulmonary lymphocytic recruitment during early M. tuberculosis infection but TNF release by lung infiltrating CD4+– and CD8+ T cells during M. tuberculosis infection is not compromised by the absence of TNF from myeloid origin.

Although TNF produced by myeloid cells regulates lung inflammation to some extent, it is not required for the initiation and maintenance of granuloma structural integrity. Because TNF is, in general, required for granuloma integrity, its non-selective depletion leads to release of granuloma-bound TB during latent infection. However TNF from macrophages is not involved in granuloma integrity and can therefore be neutralised from the system without risk of TB reactivation.

T cell derived TNF is required for sustained control of pulmonary M. tuberculosis during chronic infection. Differential regulation of inflammatory genes by myeloid versus T-cell derived TNF during acute M. tuberculosis infection has also been clearly demonstrated. Ultimately, deficiency in both myeloid- and T-cell derived TNF confers high susceptibility to M. tuberculosis infection and reconstitutes the phenotype of TNF–/– mice. This relates essentially to a situation analogous to the pan TNF blockade and enables TB reactivation and worsening of infection in patients at risk. Refer Allie et al (2013, Sci. Rep., 2013, 3: 1809) for a detailed description of the experimental approaches applied.

Generation and Evaluation of Novel Bi-Specific Reagents Capable of Neutralizing TNF on Specific Cells or in Specific Compartments Previously, the inventors have evaluated several bioengineered proteins containing TNF-binding unit from llama "nanobodies" (Coppitiers et al. 2006) expressed in various systems in mono or bi-valent forms (Plagmann et al. 2009, Conrad et al, 2010) and found them to be active in acute LPS/D-Gal toxicity model (FIG. 11). Yet additionally, recent screening of lymphocyte library prepared from immunized Camelus bactrianus (a two-hump Camel) resulted in identification of additional single domain (VHH) antibodies recognizing human TNF (Efimov et al. 2009b). These TNF-binding motifs can be fused to another protein domain that thus determines specificity of the anti-TNF targeting.

Finally, the inventors generated and tested a prototype bispecific antibody carrying two moieties, anti-hTNF and anti-mF4/80 (FIG. 12-14). This bispecific antibody A9 showed specific binding to F4/80+ macrophages isolated from peritoneal cavity (FIG. 12) and could inhibit TNF secretion from bone marrow macrophages (FIG. 13). Therefore, such antibody represents a model reagent for myeloid cell targeted TNF neutralization.

Design of Bispecific Antibody A9

Bispecific antibody A9 (sequence shown in FIG. 15A) comprises of an anti-human TNF $V_HH$ domain (according to Plagmann et al (2009), J Biotechnol 142, 170-8) joined by a GSGGGGSG linker to an anti-F4/80 scFv domain. The N-terminus of the bi-specific antibody contained a PelB leader sequence facilitating its transfer to the periplasmic space; while at the C-terminus a 6× His tag sequence was inserted to facilitate purification by immobilized metal ion affinity chromatography. The mA9 antibody used as a negative control has the same amino acid sequence as A9 except that each of the six CDRs in the anti-F4/80 scFv sequence are substituted for glycine-serine insertions of the same length (see FIG. 15B).

Expression and Purification of A9

Nucleotide sequences coding for A9 and mA9 bi-specific antibodies were cloned into pET-28b vector (Novagen, Madison, Wis.) and used to transform Rosetta2 pLysS cells. Bacterial culture was grown O/N in LB media containing 50 μg/ml Kanamycin (Sigma-Aldrich, St. Louis, Mo.-60615), 34 μg/ml Chloramphenicol (Sigma-Aldrich, St. Louis, Mo.—C1863) then it was diluted 200 times with LB contacting no antibiotic and grown at 37° C., 250 rpm until mid-log phase. It was induced with 0.2 mM IPTG and grown at 20° C. for another 4 h. Induction cultures were centrifuged at 1700 g for 30 min, S/N were discarded and pellets were frozen at −80° C. Pellets were resuspended in lysis buffer containing 50 mM Tris HCl, 300 mM NaCl, 2.5 mM MgCl2, 10 mM β-mercaptoethanol, 5% glycerol, 0.5% Triton X-100 and lysozyme 50 μg/ml with pH=8.5. 10 ml of buffer was used per gram of bacterial pellet. Solution was sonicated 4 times for 30 sec. at 70% power, 70% impulse time and then centrifuged at 17000 g, 4° C. for 30 min. After that the supernatant was filtered thought 0.22 μm filter and used for IMAC.

A9 and mA9 bi-specific antibodies were purified from supernatant containing cytoplasmic fraction using Ni-NTA resin (Pierce, Rockford, Ill.-88221) according to the manufacturer's protocol, except that all buffers were supplemented with 5 mM β-mercaptoethanol. The elution fraction containing recombinant antibodies was concentrated, dialyzed to PBS, sterile filtered and stored at +4° C. The concentration was measured by BCA assay (Pierce, Rockford, Ill.-23227) according to the manufacturer's protocol.

Cytotoxic Assay

Mouse fibrosarcoma L929 cells were plated in 96-well culture plates at 5000 cells per well. Recombinant hTNF (100 U/ml) and Actinomycin-D (4 μg/ml) were added at constant concentrations. A9 and mA9 bi-specific antibodies were applied at serial two-fold dilutions from 1 μM to 1.9 pM. After 24 h incubation MTT (4 μg/ml) was added. 16 h later OD was measured at 540 nm with a reference of 492 nm. Percentage of living cells was calculated. Nonlinear regression was fitted using Graph Pad Prism software. hTNF inhibition activity was calculated as a function of LD50 dose.

LPS/D-Galactosamine Induced Acute Hepatotoxicity Model

Female hTNF humanized mice 16 weeks of age were injected intraperitoneally (IP) with various doses of A9 and mA9 (300, 750, 1500 U/g) or PBS. 30 min later acute hepatotoxicity was stimulated by IP injection of 0.4 μg LPS and 0.8 mg D-Galactosamine (SIGMA G1639) per gram of mouse weight. Mice were observed for 24 hours. Time of death was recorded.

Experimental Results from Cytotoxic Activity and Induced Acute Hepatitis Model

Both A9 and mA9 bi-specific antibodies showed high hTNF inhibiting activity in an in vitro assay. LD50 for A9 was estimated at 809 pM, for mA9 at 509 pM. Activities were 12.5 kU/nmol and 19.5 kU/nmol respectively.

In vivo experiments showed markedly different effects for bi-specific inhibitor A9 and control antibody mA9 (FIG. 16). At a dose of 750 U/g all mice injected with mA9 succumbed while all injected with A9 survived. In dose 1500 U/g 1 out of 4 mice mA9 injected mice succumbed, and all of A9 treated mice survived (FIG. 17). This demonstrates that specific inhibition of TNF on macrophages prevents systemic toxicity. At certain higher doses mA9 may also protect mice from lethality. The exact mechanism is not yet known. TNF from macrophages is however critical in this model, which has been discussed in Grivennikov et al. (Immunity, 2005, 22(1):93-104; also refer for a description of the experimental procedures for this model).

Notably, ablation of TNF on dendritic cells (DC) does not prevent TNF-mediated toxicity (FIG. 18). Altogether, these data indicate the critical role of TNF produced by macrophages, but not DC in acute TNF-mediated pathology and, that the bi-specific A9 antibody, exhibiting both anti-macrophage and anti-TNF moieties, could specifically inhibit such activity.

Experimental Arthritis Model

Experimental arthritis was induced in C57Bl/6 (WT) mice by two immunizations with chicken collagen type II emulsified in complete Freund's adjuvant on days −21 and day 0. Infliximab, control Ig or bispecific A9 antibodies were injected once a week starting from day 12 after the 2nd immunization (twice a week for A9) at varying concentrations, using 10 mg/kg in the first round of experiments. Disease scores were determined by a pathologist. Preliminary assessment indicates that bispecific A9 antibodies show effective relief from pathological symptoms in an experimental arthritis model, under some conditions at comparatively lower doses than Infliximab. Further analysis in this or other arthritis models (such as described in more detail in Rosloniec et al. 2010, Current Protocols in Immunology, 89:15.5.1-15.5.25, or Rioja et al., 2004, Clin Exp Immunol., 137(1): 65-73) may be conducted in order to assess subject response after treatment with the antibodies of the invention.

REFERENCES

1. Grivennikov, S. I., Tumanov, A. V., Liepinsh, D. J., Kruglov, A. A., Marakusha, B. I., Shakhov, A. N., Murakami, T., Drutskaya, L. N., Förster, I., Clausen, B. E., Tessarollo, L., Ryffel, B., Kuprash, D. V., and Nedospasov, S. A. Distinct and non-redundant in vivo functions of TNF produced by T cells and macrophages/neutrophils: protective and deleterious effects. Immunity 2005, 22: 93-104.
2. Kuprash, D. V., Tumanov, Grivennikov, S. I., Kruglov, Koroleva, E. P., Drutskaya, M. S., Shakhov, A. N., Southon, E., Tessarollo, L., and Nedospasov, S. A. Novel tumor necrosis factor knockout mice that lack Peyer's patches. Eur J. Immunol. 2005, 35: 1592-1600.
3. Efimov, G. A., Kruglov, A. A., Tillib, S. V., Kuprash, D. V. and Nedospasov, S. A. Tumor Necrosis Factor and the consequences of its ablation in vivo. Mol. Immunol. 2009, 47: 19-27.
4. Plagmann, I., Chalaris, A., Kruglov, A. A., Nedospasov, S. A., Rosenstiel, P., Rose-John, S., and Scheller, J. Transglutaminase-catalyzed covalent multimerization of Camelidae anti-human TNF single domain antibodies improves neutralizing capacity of human TNF. J. Biotechnol. 2009, 142: 170-178.
5. Conrad, U., Plagmann, 1., Malchow, 5., Sack, M., Floss, D. M., Kruglov, A. A., Nedospasov, S. A., Rose-John, S., and Scheller, J. EGPylated anti-human TNF-therapeutic single domain antibodies for prevention of lethal septic shock. Plant J. of Biotechnol. 2010 (published on-line April 20).
6. Tumanov, A. V., Grivennikov, S. I., Kruglov, A. A., Shebzukhov, Y. V., Piao, Y., Cui, C.-Y., Kuprash, D. V., and Nedospasov, S. A. Cellular source and molecular form of TNF specifies its distinct functions in the development and maintenance of secondary lymphoid tissues. Blood, 2010 (116: 3456-64).
7. Anolik, J. H., Ravikumar, R., Barnard, J., Owen, T., Almudevar, A., Milner, E. C., Miller, C. H., Dutcher, P. O., Hadley, J. A. and Sanz, I., Cutting edge: anti-tumor necrosis factor therapy in rheumatoid arthritis inhibits memory B lymphocytes via effects an lymphoid germinal centers and follicular dendritic cell networks. J Immunol 2008. 180: 688-692.
8. Coppieters, K., Dreier, T., Silence, K., de Haard, H., Lauwereys, M., Casteels, P., Beimaert, E., Jonckheere, H., Van de Wiele, C., Staelens, L., Hostens, J., Revets, H., Remaut, E., Elewaut, D. and Rottiers, P., Formatted anti-tumor necrosis factor alpha VHH proteins derived from camelids show superior potency and targeting to inflamed joints in a murine model of collageninduced arthritis. Arthritis Rheum 2006. 54: 1856-1866.
9. Eisenberg, R. and Albert, D., B-cell targeted therapies in rheumatoid arthritis and systemic lupus erythematosus. Nat Clin Pract Rheumatol 2006. 2: 20-27.
10. Endres R., Alimzhanov M. B., Plitz T., Fuetterer A., Kosco-Vilbois M. H., Nedospasov S. A., Rajewsky K., and Pfeffer K. Mature follicular dendritic cell networks depend an expression of lymphotoxin beta receptor by radioresistant stromal cells and of lymphotoxin beta and Tumor Necrosis Factor by B cells. 1999. J. Exp. Med. 189, 159-168.
11. Ehrenstein, M. R., Evans, J. G., Singh, A., Moore, S., Warnes, G., Isenberg, D. A. and Mauri, C., Compromised function of regulatory T cells in rheumatoid arthritis and reversal by anti-TNFalpha therapy, J Exp Med 2004. 200: 277-285.
12. Hobeika E, Thiemann S, Storch B, Jumaa H, Nielsen P J, Pelanda R, and Reth M. Testing gene function early in the B cell lineage in mbl-cre mice. Proc Natl Acad Sci USA. 2006 103: 13789-13794.
13. Hughes, C., Faurholm, B., Dell'Accio, F., Manzo, A., Seed, M., Eltawil, N., Marrelli, A., Gould, D., Subang, C., Al-Kashi, A., De Bari, C., Winyard, P., Chernajovsky, Y., and Nissim, A. Human single-chain variable fragment that specifically targets arthritic cartilage. Arthritis Rheum 2010. 62: 1007-1016.
14. Kuprash D. V. Alimzhanov M. B., Tumanov A. V., Shakhov, A. N., Grivennikov S.1., Marino, M. W., Turetskaya, R. L., Anderson A. O., Rajewsky K., Pfeffer K. and Nedospasov S. A. Redundancy in TNF and LT signaling in vivo: mice with inactivation of the entire TNF/LT locus versus single knockout mice. 2002. Mol. Cell Biol. 22: 8626-8634.
15. Lakey, R. L., Morgan, T. G., Rowan, A. D., Isaacs, J. D., Cawston, T. E. and Hakens, C. M., A novel paradigm for dendritic cells as effectors of cartilage destruction. Rheumatology (Oxford) 2009. 48: 502-507.
16. Liepinsh, D. J., Kruglov, A. A., Galimov, A. R., Shebzukhov, Yu. V., Tumanov A. V., Grivennikov, S. I., Drutskaya, M. S., Feigenbaum, L., Shakhov, A. N., Kuprash, D. V., and Nedospasov, S. A. Thymic athrophy due to homeostatic overexpression of TNF/LT cytokines. Eur. J. Immunol. 2009. 39: 2906-2915.
17. Notley, C. A., Inglis, J. J., Alzabin, S., McCann, F. E., McNamee, K. E. and Williams, R. O., Blockade of tumor necrosis factor in collagen-induced arthritis reveals a novel immunoregulatory pathway for Th1 and Th17 cells. J Exp Med 2008. 205: 2491-2497.
18. Radko, B., Boitchenko, V. E., Nedospasov, S. A. and Korobko, V. G. Characterization of the variable light and heavy chain genes of high-affinity monoclonal antibody against human Tumor Necrosis Factor. 2002. Russ. J. Immunof. 7, 371-374.
19. Ruuls, S. R., Hoek, R. M., Ngo, V. N., McNeil, T., Lucian, L. A., Janatpour, M. J., Korner, H., Scheerens, H., Hessel, E. M., Cyster, J. G., McEvoy, L. M., and Sedgwick, J. D. (2001). Membrane-bound TNF supports secondary lymphoid organ structure but is subservient to secreted TNF in driving autoimmune inflammation. Immunity. 15, 533-543.
20. Taylor, P. C., Williams, R. O. and Maini, R. N., Anti-TNF alpha therapy in rheumatoid arthritis—current and future directions. Curr Dir Autoimmun 2000.2: 83-102.
21. Yoshina, S., Cleland L., and Mayrhofer, G. Treatment of collagen-induced arthritis in rats with a monoclonal antibody against the alpha/beta T cell antigen receptor. Arthritis Rheum. 1991 34:1039-47.
22. Zvaifler, N. J., Steinman, R. M., Kaplan, G., Lau, L. L., and Rivelis, M. Identification of immunostimulatory dendritic cells in the synovial effusions of patients with rheumatoid arthritis. J Clin Invest. 1985. 76: 789-800.
23. Kruglov A A, Lampropoulou V, Fillatreau S, Nedospasov S A. Pathogenic and protective functions of TNF in neuroinflammation are defined by its expression in T lymphocytes and myeloid cells. J Immunol. 2011. 187: 5660-70.
24. Allie N., Grivennikov S. I., Keeton, R., Hsu, N-J., Bourigault, M.-L., Court, N., Fremond, C., Yeremeev, V. V., Shebzukhov, Yu. V., Ryffel, B., Nedospasov, S. A., Quesniaux, V., and Jacobs M., Prominent role of T cells-derived Tumor Necrosis Factor for sustained control of *Mycobacterium tuberculosis* infection. Sci. Rep., 2013, 3: 1809.

The invention claimed is:

1. An isolated bispecific antibody or antibody fragment comprising:
one or more amino acid sequences that specifically bind TNFα and
a marker molecule for macrophages and/or neutrophils, wherein the isolated bispecific antibody or antibody fragment predominantly binds and/or neutralizes said TNFα produced in said macrophages and/or said neutrophils compared to further TNFα produced in other cell types.

2. The isolated bispecific antibody or antibody fragment according claim 1, wherein further TNFα produced in cell types other than macrophages and neutrophils is bound and/or neutralized to a reduced extent in comparison to a monospecific TNFα antibody or antibody fragment.

3. The isolated bispecific antibody or antibody fragment according to claim 1, wherein the further TNFα produced in T cells is bound and/or neutralized to a reduced extent in comparison to a monospecific TNFα antibody or antibody fragment.

4. The isolated bispecific antibody or antibody fragment according to claim 1, wherein the marker molecule for the macrophages and/or the neutrophils is F4/80 (EMR1), CD163, CD169 or Mer Tk.

5. The isolated bispecific antibody or antibody fragment according to claim 1, wherein the isolated bispecific antibody or antibody fragment is a chimeric, humanized or single chain antibody, or a combination thereof.

6. The isolated bispecific antibody or antibody fragment according to claim 1, wherein the isolated bispecific antibody or antibody fragment comprises, one or more amino acid sequences that specifically bind
TNFα and
F4/80 (EMR1).

7. The isolated bispecific antibody or antibody fragment according to claim 1, wherein a TNFα binding domain comprised in said antibody or antibody fragment is a single domain antibody or antibody fragment.

8. The isolated bispecific antibody or antibody fragment according to claim 7, wherein, the single domain is a VHH domain, comprising
a sequence according to SEQ ID No. 1 (MGSQVQLQESGGGLVQPGGSLRLSCAASGRTFSDHSGYTYTIGWFRQAPGK REFVARIYWSSGNTYYADSVKGRFAISRDIAKNTVDLTMNNLEPEDTAVYYCA ARDGIPTSRSVESYNYWGQGTQVTVSSAGA).

9. The isolated bispecific antibody or antibody fragment according to claim 6, comprising an anti-F4/80 or anti-EMR1 binding domain that comprises a single chain variable fragment (scFv).

10. The isolated bispecific antibody or antibody fragment according to claim 9, wherein the single chain variable fragment (scFv) comprises
a VH domain comprising CDR H1 (SEQ ID No. 2: GYTFTNHMN), CDR H2 (SEQ ID No. 3: RINPGTGGTSYNVNFKG) and CDR H3 (SEQ ID No. 4: GDSYWYFDF) and
a VL domain comprising CDR L1 (SEQ ID No. 5: KASKSISKYLA), CDR L2 (SEQ ID No. 6: EGSTLQS) and CDR L3 (SEQ ID No. 7: QQHNEYPLT).

11. The isolated bispecific antibody or antibody fragment according to claim 1 comprising
a VH domain comprising a sequence according to SEQ ID No. 8 (MQVQLQQSGAELVKPGTSVKLSCKASGYTFTNHMNWVKQTTGQGLEWIGRIN PGTGGTSYNVNFKGKATLTVDESSSTAFMQLSSLTPEDSAVYYCARGDSYWYF DFWGPGTMVTVSGS) and
a VL domain comprising a sequence according to SEQ ID No. 9 (DVQMTQSPYNLVASPGESVSINCKASKSISKYLAWYQQKPGKANKLLIYEGSTL QSGIPSRFSGSGSGTDFTLTIRSLEPEDFGLYYCQQHNEYPLTFGSGTKLEIKRA DAAPTVAAAPRGGPEQKLISEEDLNSAVD).

12. The isolated bispecific antibody or antibody fragment according to claim 1 comprising a sequence according to SEQ ID No. 10 or 21.

13. The isolated bispecific antibody or antibody fragment according to claim 1, wherein the bispecific antibody or antibody fragment is part of a medicament.

14. Pharmaceutical composition comprising the isolated bispecific antibody or antibody fragment according to claim 1, together with a pharmaceutically acceptable carrier.

15. A method for treating a medical disorder associated with a macrophage and/or neutrophil TNFα-mediated inflammation, comprising:
administering a therapeutically effective amount of a bispecific antibody or antibody fragment according to claim 1 to a patient in need of said treatment.

16. The method of claim 15, wherein said medical disorder is arthritis.

17. The method of claim 15, wherein said medical disorder is acute hepatitis.

18. An isolated nucleic acid molecule comprising:
a) a nucleic acid molecule comprising a nucleotide sequence encoding a bispecific antibody or antibody fragment comprising:
one or more amino acid sequences that specifically bind TNFα and
a marker molecule for macrophages and/or neutrophils, wherein the isolated bispecific antibody or antibody fragment predominantly binds and/or neutralizes said TNFα produced in said macrophages and/or said neutrophils compared to further TNFα produced in other cell types;
b) a nucleic acid molecule comprising a nucleotide sequence encoding the amino acid sequence of:
(i) SEQ ID No. 1 and SEQ ID Nos. 2-7,
(ii) SEQ ID No. 1 and SEQ ID Nos. 8-9,
(iii) SEQ ID No. 10, or
(iv) SEQ ID No. 21; or
c) a nucleic acid molecule which is complementary to a nucleotide sequence in accordance with a) or b).

19. A host cell comprising a nucleic acid molecule according to claim 18, wherein the host cell expresses a bispecific antibody or antibody fragment comprising one or more amino acid sequences that specifically bind TNFα and a marker molecule for macrophages and/or neutrophils, wherein the isolated bispecific antibody or antibody fragment predominantly binds and/or neutralizes said TNFα produced in said macrophages and/or said neutrophils compared to further TNFα produced in other cell types.

* * * * *

UNITED STATES PATENT AND TRADEMARK OFFICE
CERTIFICATE OF CORRECTION

PATENT NO. : 9,688,757 B2
APPLICATION NO. : 14/438288
DATED : June 27, 2017
INVENTOR(S) : Nedospasov et al.

It is certified that error appears in the above-identified patent and that said Letters Patent is hereby corrected as shown below:

On the Title Page

Under abstract "19 Claims, 15 Drawing Sheets" should read -- 19 Claims, 16 Drawing Sheets --

In the Drawings

After sheet 15 of Drawings, insert sheet 16 containing -- Figs. 17-18 -- as shown on the attached sheet Signed and Sealed this
Nineteenth Day of December, 2017

Joseph Matal
*Performing the Functions and Duties of the*
*Under Secretary of Commerce for Intellectual Property and*
*Director of the United States Patent and Trademark Office*